(12) United States Patent
Cornelius

(10) Patent No.: US 9,678,367 B2
(45) Date of Patent: Jun. 13, 2017

(54) MULTI-PANE, MULTI-GEOMETRY GOGGLE EYE-SHIELD

(71) Applicant: Abominable Labs, LLC, Lake Oswego, OR (US)

(72) Inventor: Jack C. Cornelius, Lake Oswego, OR (US)

(73) Assignee: Abominable Labs, LLC, Lake Oswego, OR (US)

( * ) Notice: Subject to any disclaimer, the term of this patent is extended or adjusted under 35 U.S.C. 154(b) by 293 days.

(21) Appl. No.: 14/479,154

(22) Filed: Sep. 5, 2014

(65) Prior Publication Data

US 2016/0070120 A1    Mar. 10, 2016

(51) Int. Cl.
  *H05B 1/00* (2006.01)
  *G02C 11/08* (2006.01)
  *A61F 9/02* (2006.01)

(52) U.S. Cl.
  CPC ............. *G02C 11/08* (2013.01); *A61F 9/029* (2013.01)

(58) Field of Classification Search
  CPC . G02C 11/08; A61F 9/02; A61F 9/028; A61F 9/026; A61F 9/025; A61F 9/029; A42B 3/185
  See application file for complete search history.

(56) References Cited

U.S. PATENT DOCUMENTS

| | | | |
|---|---|---|---|
| 4,150,443 A | 4/1979 | McNeilly | |
| 4,209,234 A | 6/1980 | McCooeye | |
| 4,443,893 A | 4/1984 | Yamamoto | |
| 5,452,480 A | 9/1995 | Ryden | |
| 5,459,533 A | 10/1995 | McCooeye et al. | |
| 5,471,036 A | 11/1995 | Sperbeck | |
| 5,815,235 A | 9/1998 | Runckel | |
| 6,704,944 B2 | 3/2004 | Kawainshi et al. | |
| 6,732,383 B2 | 5/2004 | Cleary et al. | |
| 6,772,448 B1 | 8/2004 | Hockaday et al. | |
| 7,810,174 B2 | 10/2010 | Matera | |
| 7,856,673 B2 | 12/2010 | Reed | |
| 2008/0290081 A1 | 11/2008 | Biddell | |
| 2009/0151057 A1 | 6/2009 | Lebel et al. | |
| 2011/0225709 A1 | 9/2011 | Saylor et al. | |
| 2014/0033408 A1* | 2/2014 | Currens ................... | A61F 9/025 2/431 |

FOREIGN PATENT DOCUMENTS

WO    WO2012178049 A1    12/2012

* cited by examiner

*Primary Examiner* — Shawntina Fuqua
(74) *Attorney, Agent, or Firm* — Howard Russell

(57) ABSTRACT

A multi-pane, multi-geometry eye-shield adapted to be installed into a frame of an eye-shield, such as a goggle for protecting user's eyes, comprising a spherical anterior outer eye-shield member, a cylindrical posterior inner eye-shield member, an irregular-shaped gasket member between the anterior and posterior eye-shield members forming a water-tight and air-tight semi-annular space therebetween. The posterior cylindrical inner eye-shield member may further be adapted for heating to reduce condensation comprising a thin-film, electrically conductive heating element, such as Indium Tin Oxide (ITO), and electrical contact members to connect the thin-film heating element to a power source.

11 Claims, 25 Drawing Sheets

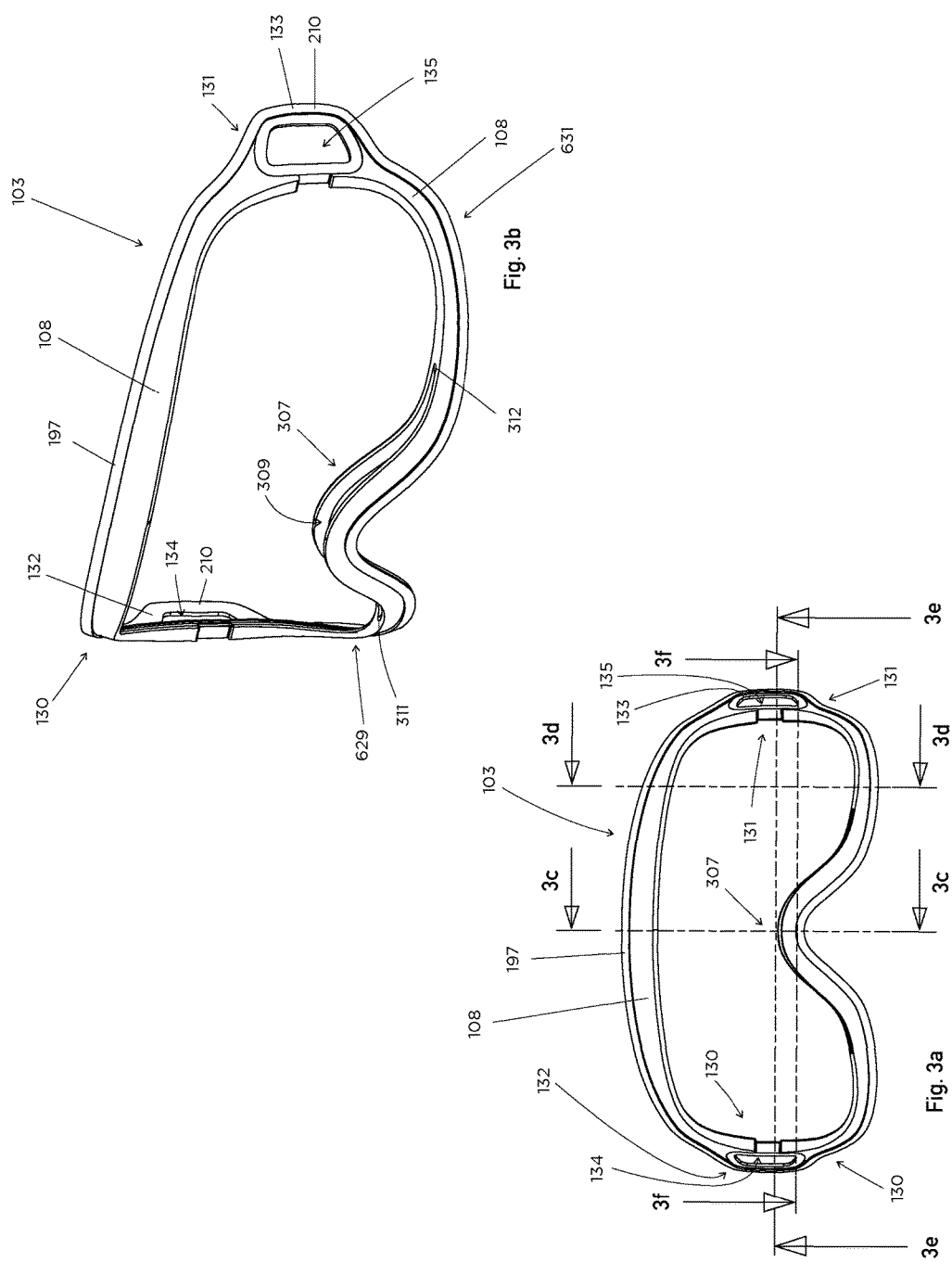

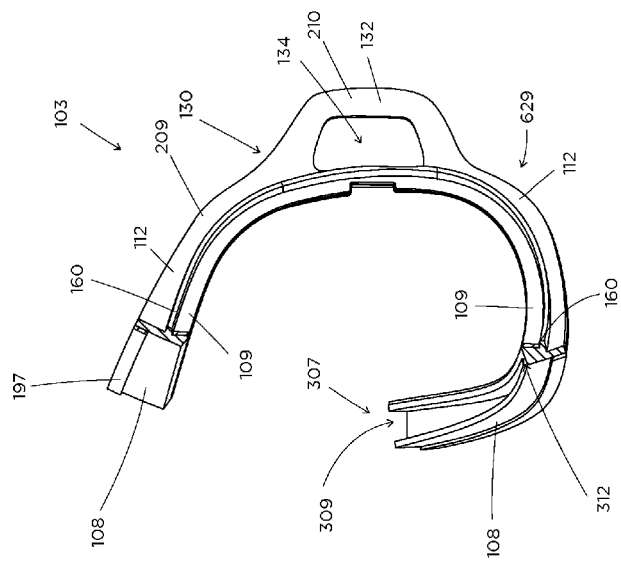
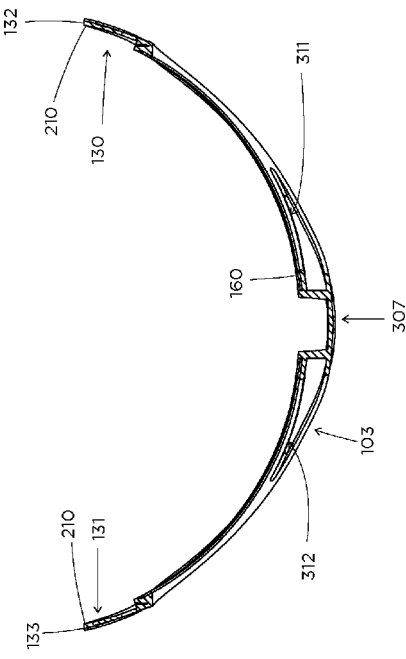
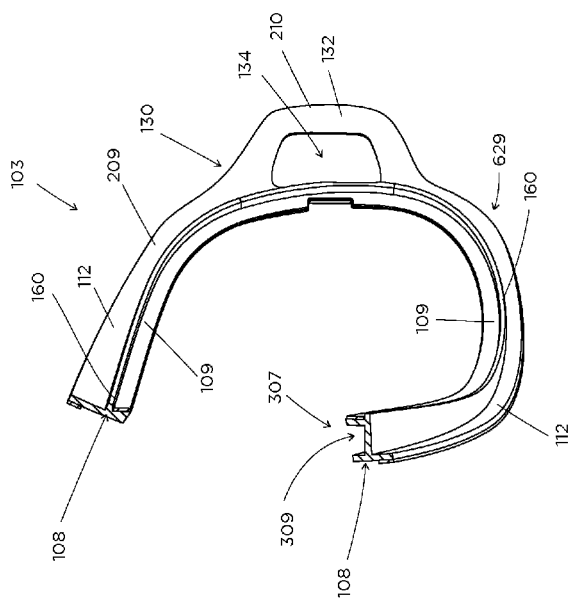
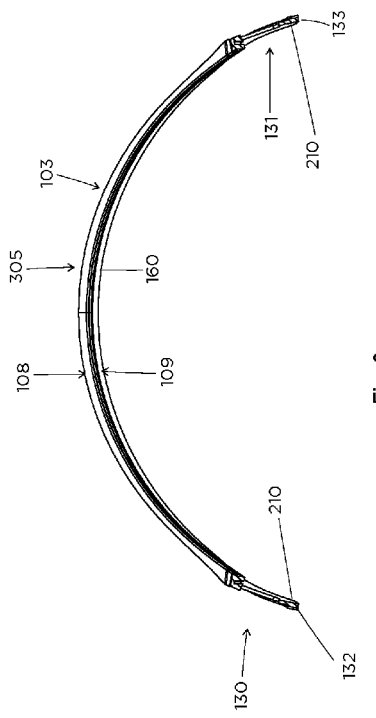
Fig. 3d
Fig. 3f
Fig. 3c
Fig. 3e

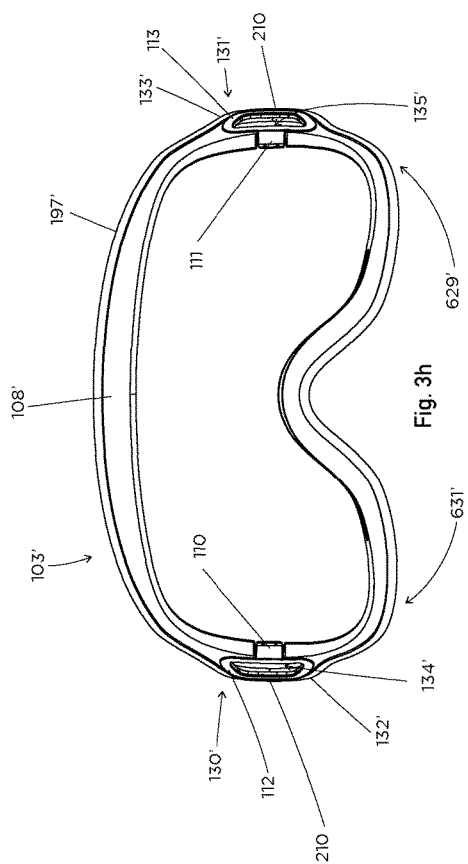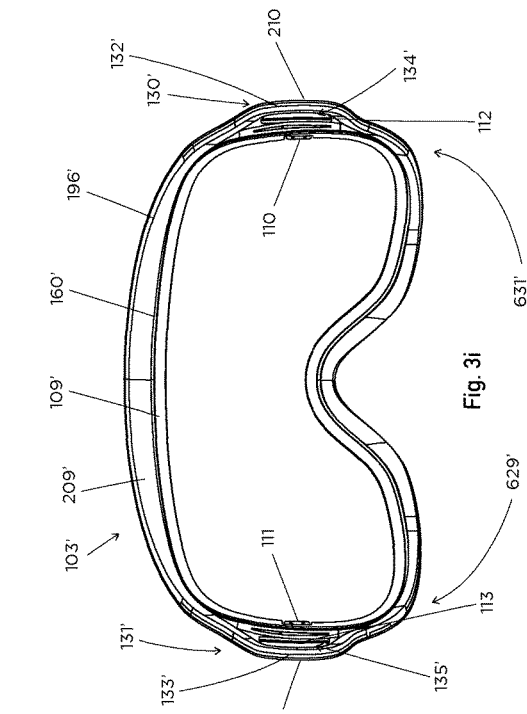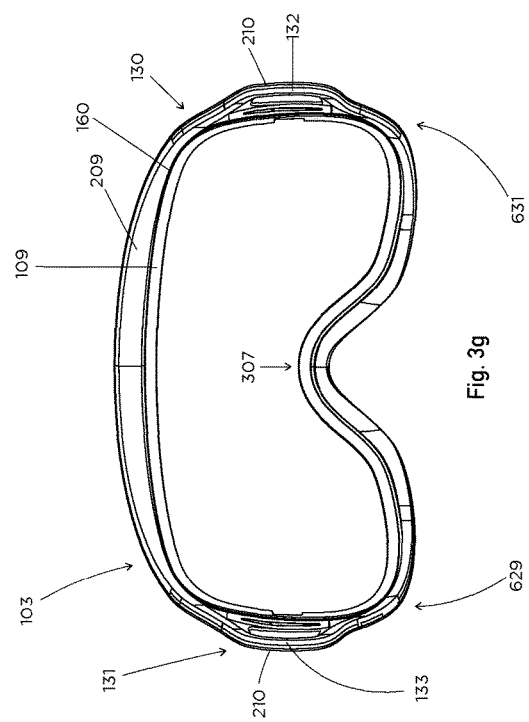

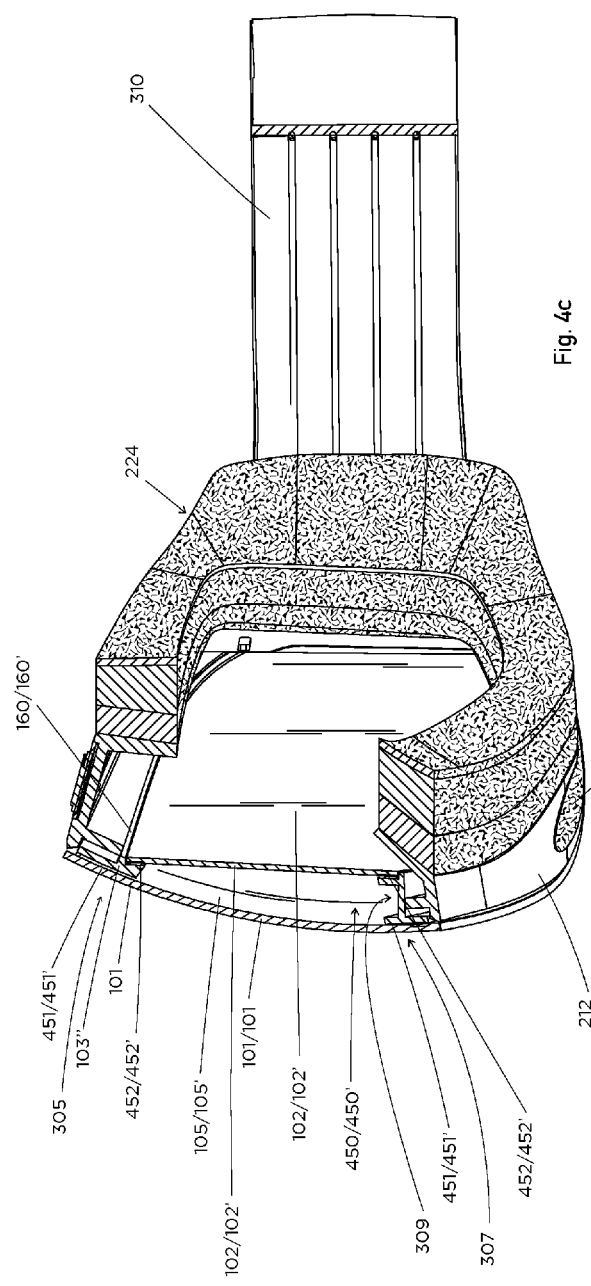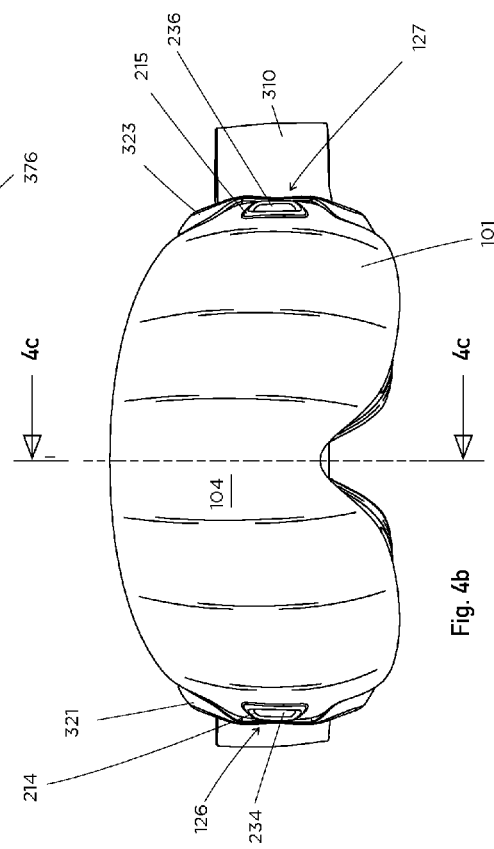

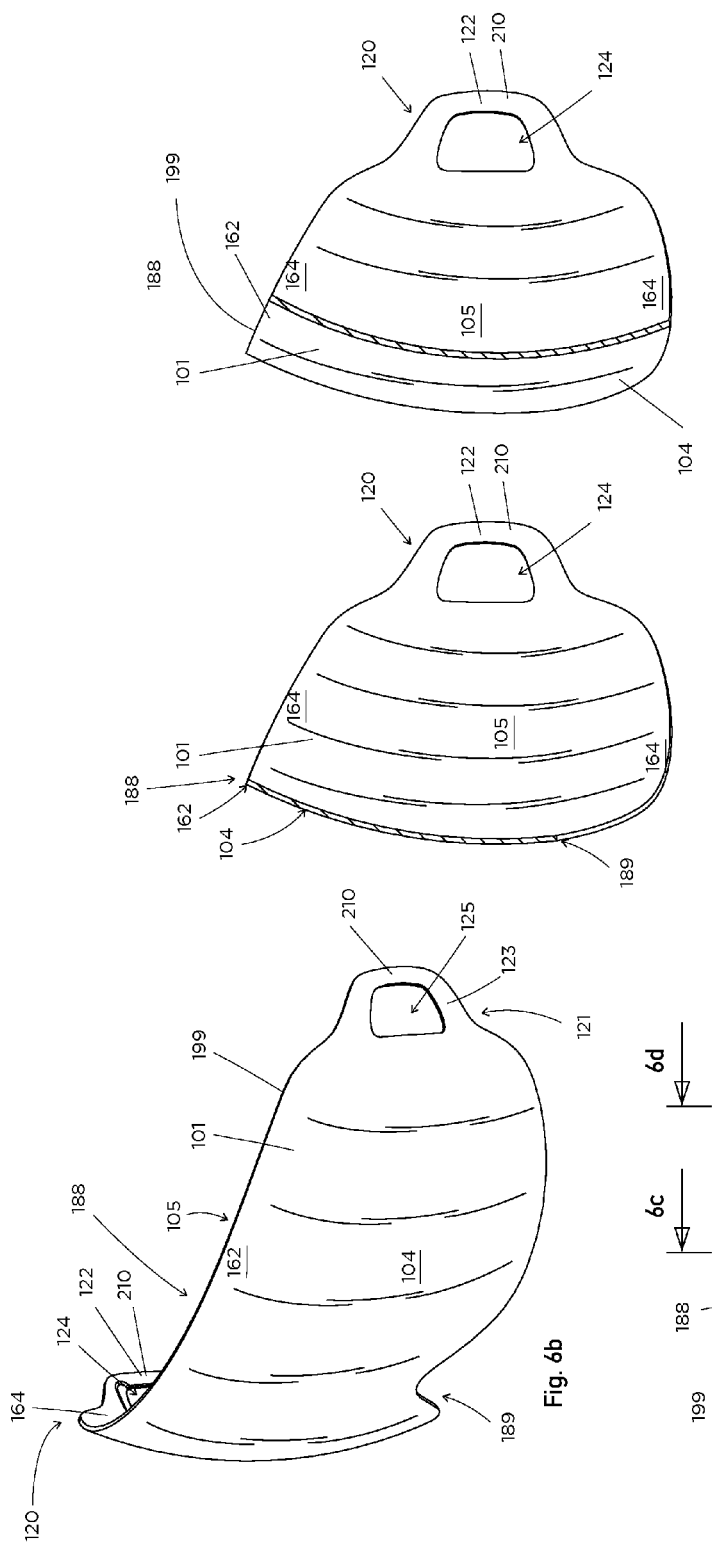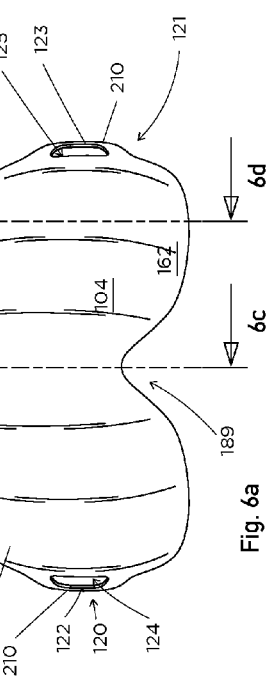

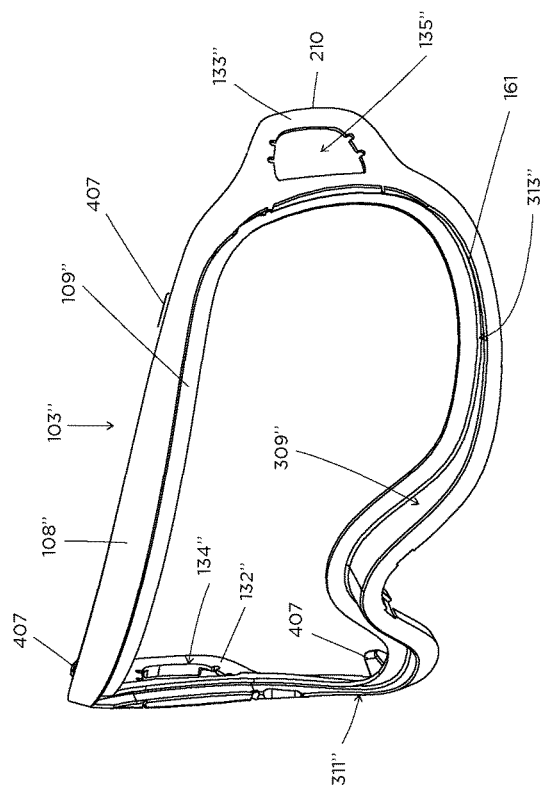
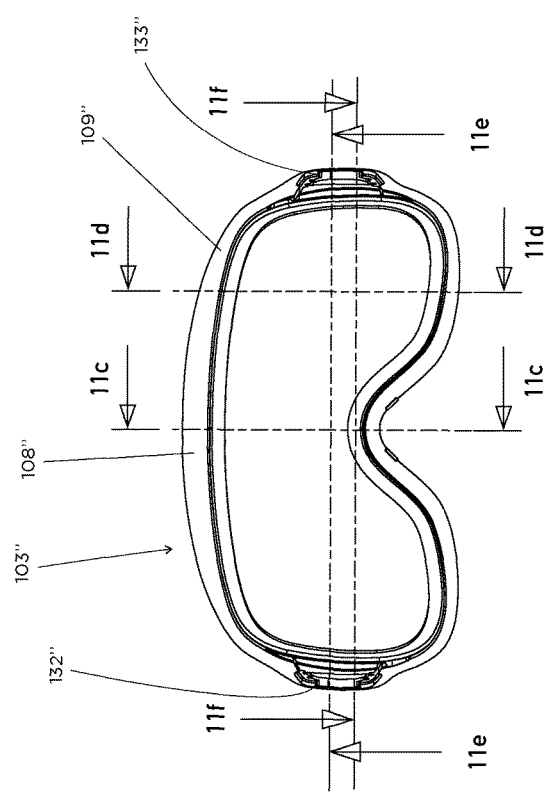
Fig. 11b
Fig. 11a

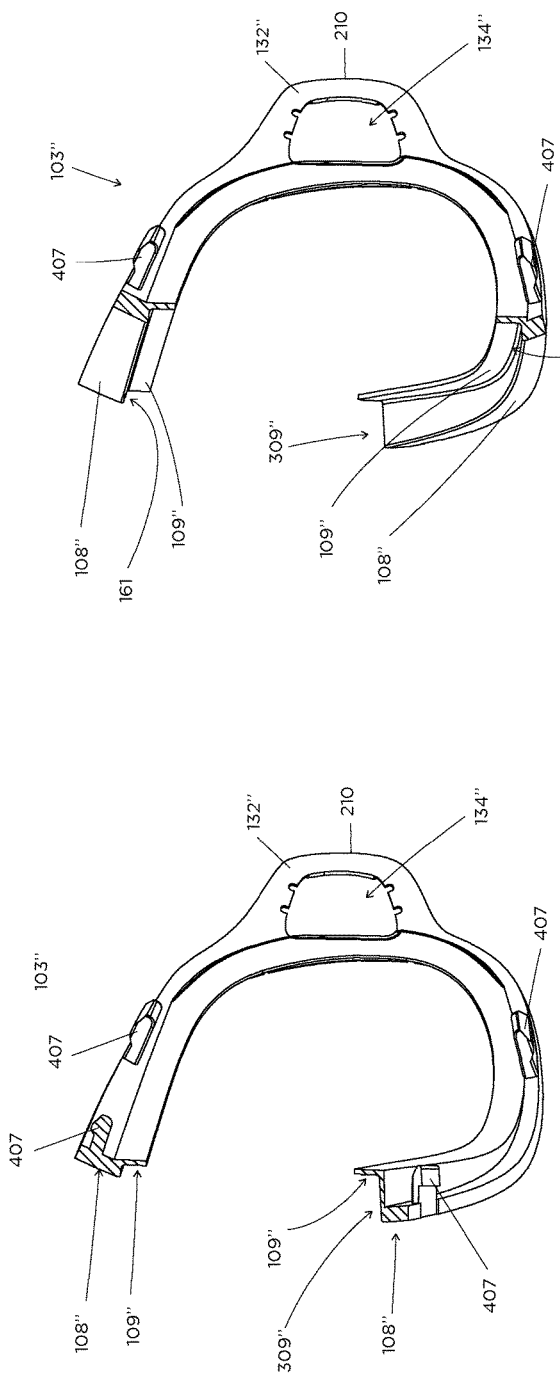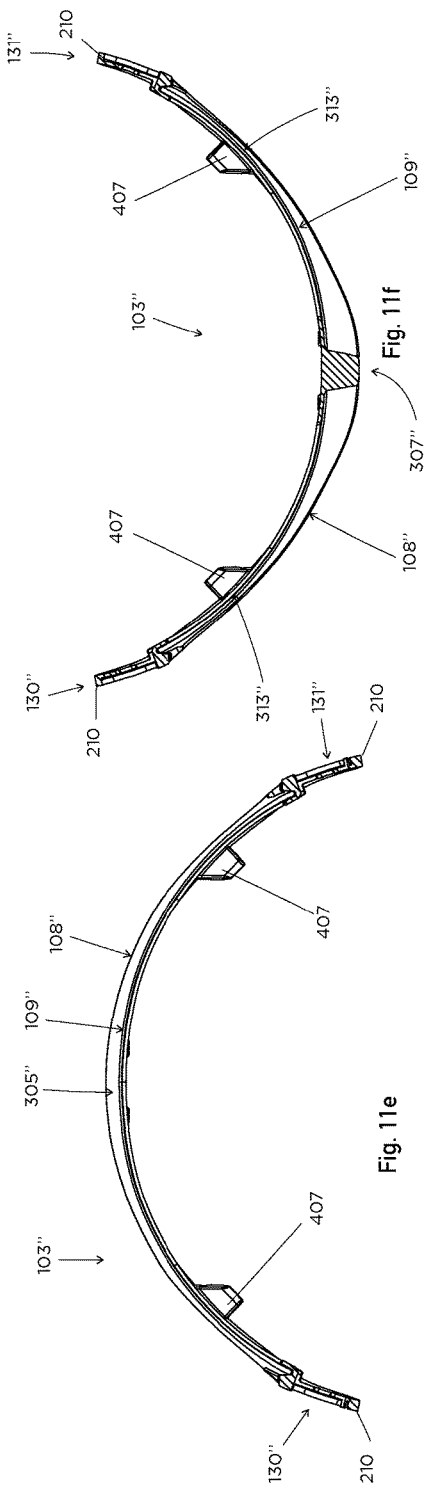

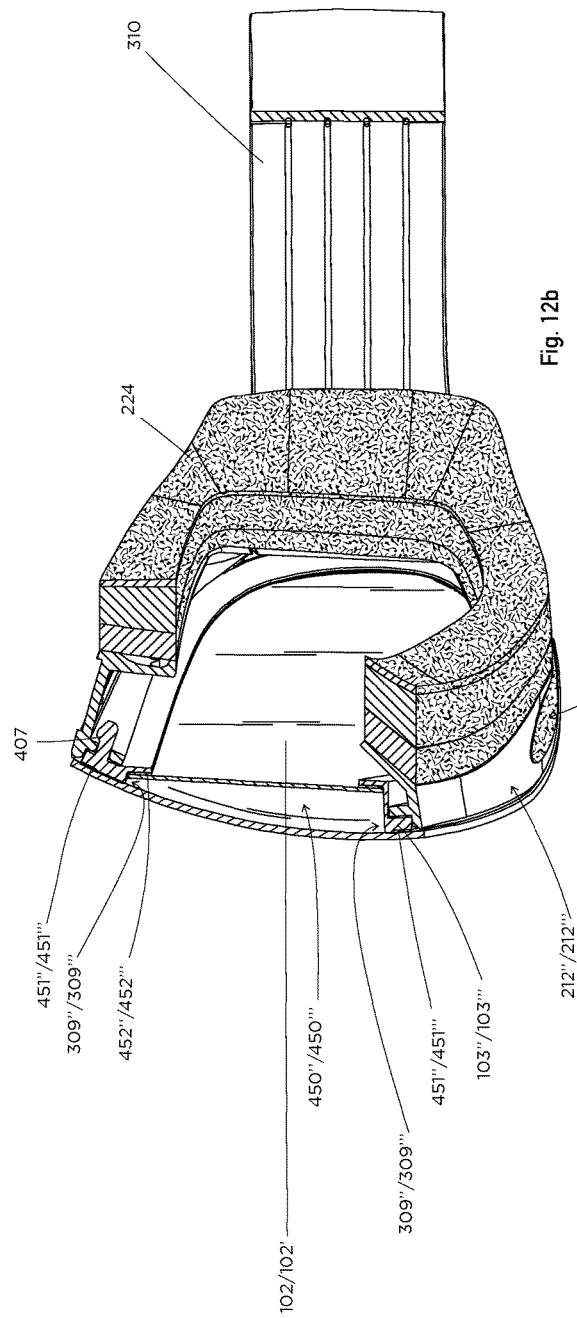
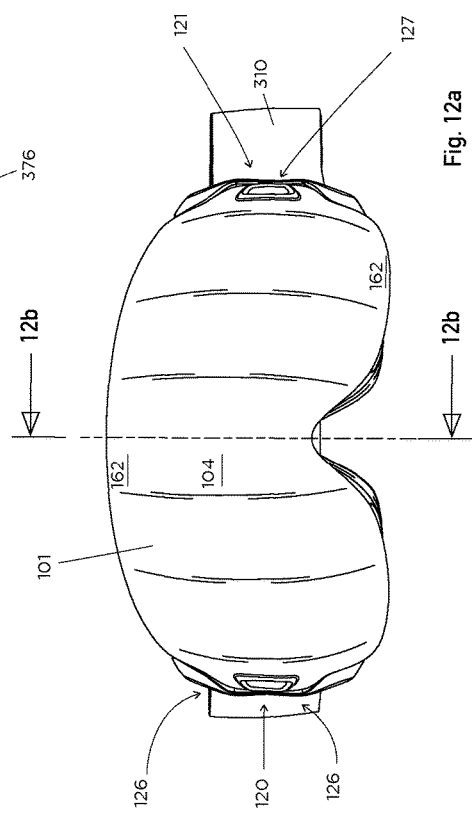
Fig. 12b
Fig. 12a

MULTI-PANE, MULTI-GEOMETRY GOGGLE EYE-SHIELD

FIELD OF THE INVENTION

This invention relates to multi-pane eye-shield goggles and multi-pane eye-shields adapted to be interchangeably installed by a user in eye-protecting eye-shield frames and more particularly to a multi-pane, multi-geometry eye-shield optionally adaptable for heating to prevent fogging and adapted for interchangeable user installation, or optionally more permanent inclusion in a non-interchangeable lens goggle system, on a goggle or a mask such as may be used for outdoor winter sports, skiing, hiking, mountaineering, climbing, ice climbing, snowboarding, snowmobiling, paintballing, swimming, scuba diving, snorkeling, hazardous activities requiring safety eye protection, industrial use, target shooting, police work, tactical operations, riot control, corrections or military use.

BACKGROUND OF THE INVENTION

It is often desirable to use goggles or protective eye-shield masks for protecting one's vision from invasion of the eyes by snow, ice, precipitation or other elements such as airborne or wind-blown particles, and also to enable clear vision during participation in various activities such as outdoor winter sports, skiing, hiking, sledding, tubing, mountaineering, climbing, ice climbing, snowboarding, snowmobiling, paintballing, swimming, scuba diving, snorkeling, hazardous activities requiring safety eye protection, industrial use, target shooting, police work, tactical operations, riot control, corrections or military use. It is also often necessary to use such goggles or masks in environments involving conditions which contribute to condensation build-up on the eye-shield and where even momentary impairment of vision by fogging would be problematic. In such environments, when the temperature of such an eye-shield drops below a dew-point temperature, i.e., the atmospheric temperature below which water droplets begin to condense and dew can form, fogging occurs.

Thus, fogging that impairs vision is a common problem with such goggles and masks, and there have been various conductive apparatus devised for preventing condensation build-up on eye-shields for eye-protecting shields. The purpose of these conductive apparatus has been to provide an eye-shield that may be maintained free of condensation so that the user would be able to enjoy unobstructed vision during viewing activities. Prior goggles with electronic systems that have been primarily used in environments requiring a high degree of portability have included a thin-film heating element, such as Indium Tin Oxide (ITO) or other thin-film heating element, on a lens that is used in a goggle having a power source carried on the frame or strap of the goggle for powering the electronics for the goggle such as has been shown and described in co-pending U.S. patent application Ser. No. 61/563,738, by McCulloch, for Modular Anti-fog Goggle System.

There are currently two different types of commonly available goggle or protective eye-shield lens form factors for protecting one's vision from invasion of the eyes by snow, ice, precipitation or other elements such as airborne or wind-blown particles: those having a cylindrical eye-shield or lens, and those having a spherical, or toric, eye-shield or lens. The first type of commonly available goggles and protective eye-shield masks has a cylindrical eye-shield. Cylindrical eye-shields are common in goggles and eye-shield masks because they have been generally less expensive and easier to manufacture. This advantage in lower-cost manufacturing has come with at least a somewhat perceived cost to wearers of cylindrical eye-shields however. Some Cylindrical eye-shields have been claimed by some to impair, impede, or distort the vision of the wearer. Some Cylindrical eye-shields also have been claimed by some to create a limited viewing window for wearers, concentrating their field of vision to what is directly in front of them. Additionally, because of the flat surface of the cylindrical eye-shield, light enters the lens at different angles which is considered by some to distort the image that the wearer sees and to create glare. These disadvantages have created a potential for hazards. Cylindrical eye-shields have also recently been determined by the Applicant to have advantageous properties when used in connection with lens heating systems.

The second, currently more fashionable, appealing to the eye and desirable type of commonly available goggle has a spherical, or toric, eye-shield. Although spherical eye-shields have been somewhat more difficult and expensive to design and manufacture, they are currently considered more fashionable and desirable than cylindrical eye-shields because some have been reputed as providing wearers with better comfort, a higher quality image, and an overall more pleasing appearance and enjoyable experience. Some claim that because the surface of spherical eye-shields comprise curved convex outer surfaces and concave inner surfaces, they conform better to the natural curves of a human head, allowing the wearer a tighter and more uniform fit. Assuming an optical-grade quality level, spherical eye-shields are also said by some to allow light to pass through them in more of a straight line, creating a less distorted image than that of a cylindrical eye-shield. An additional benefit to spherical eye-shields is they may help to prevent glare, or are at least perceived as doing so by some, lessening the potential for hazards than may otherwise be the case with cylindrical eye-shields. Thus, spherical lens eye-shields have been more fashionable and desirable for wearers of goggles.

When applying ITO to eye-shields for use as a thin film-heating element, it is important to achieving even heating (at least given a uniform eye-shield surface area) that the ITO is applied uniformly across the surface of the eye-shield. Absent intentional design for irregular-shaped lenses as described in co-pending U.S. patent application Ser. No. 14/040,683, by Cornelius, for Multiregion Heated Eye Shield, an irregular coating of ITO on the surface will create an undesirable uneven resistance in the material and result in undesirable uneven heating. Applying a substantially even coat of ITO across the surface of a cylindrical eye-shield has been relatively simple and cost effective to design and manufacture, since the ITO has been applied by a film backing or ion sputtering to a flat surface lens, which has then later been shaped to form a cylindrical lens. Or alternatively, the ITO may have been deposited relatively easily on the inner cylindrical surface with a film backing or by ion sputtering, as the case may be. It is apparent therefore, that the relatively easier and cost effective process of applying ITO to a cylindrical lens has not allowed easy production of a heated lens that is also more desirable and spherical, or toric, in shape. Thus there has developed a need in the industry for a cost effective way to provide a thin-film heated lens for a goggle or eye-shield mask that is also spherical and currently fashionable and desirable.

SUMMARY OF THE INVENTION

In accordance with an embodiment of a first aspect of the invention, there is provided a multi-pane, multi-geometry eye-shield adapted to be installed into a frame of an eye-shield apparatus, such as a goggle. The eye-shield in accordance with this aspect of the invention comprises: a spherical anterior outer eye-shield member having an anterior convex substantially spherical, or toric, surface and peripheral area and a posterior concave substantially spherical, or toric, surface and peripheral area. It will be appreciated that references herein to spherical, toric or cylindrical lenses, eye-shields or gasket surfaces, actually refer to a partial sphere, partial torus or partial cylinder on each of these elements, respectively, not that the elements comprise an entire sphere, torus or cylinder. Also, the term "spherical" is often used herein, but it will be appreciated that "toric" would also apply without departing from the true scope and spirit of the invention. Thus, the terms "spherical", "toric" and "cylindrical", as used herein, refer to the shape of the element at the given location being described, not that the element comprises an entire sphere, torus or cylinder. The eye-shield in accordance with this aspect of the invention further comprises: a cylindrical posterior inner eye-shield member having an anterior convex substantially cylindrical surface and peripheral area and a posterior concave substantially cylindrical surface and peripheral area, and a semi-annular, or quasi-annular, gasket member ring (typically generally in the shape of a peripheral edge of a goggle lens) interposed between the anterior and posterior eye-shield members preferably forming a water-tight and air-tight semi-annular space between the eye-shield members. The gasket member is semi-annular, or quasi-annular, not in the sense that it is only a partial annulus, but in the sense that it is typically not perfectly circular but still typically contains a plurality of complex curves around it's periphery. So while the gasket typically does not comprise a perfect circular loop, it nevertheless may preferably comprise a contiguous member formed in the shape of a somewhat irregular loop, for example in the shape of a goggle lens periphery as shown in FIGS. 3 and 11. The gasket member has an anterior spherical, or tonic, peripheral surface adapted for interfacing to the concave spherical, or toric, posterior surface, or peripheral area, respectively, of the spherical anterior eye-shield member, and the gasket also has a posterior concave cylindrical peripheral surface adapted for interfacing to the convex cylindrical anterior surface peripheral area of the cylindrical posterior eye-shield member. The posterior eye-shield member is posterior relative to the anterior eye-shield member and at least part of the gasket, not the entire eye-shield apparatus including an eye-shield apparatus frame member.

In accordance with another embodiment of this first aspect of the invention, there is provided a multi-pane, multi-geometry eye-shield adapted to be installed into a frame of a goggle, comprising: a spherical anterior outer eye-shield member having an anterior convex substantially spherical, or toric, surface and peripheral area and a posterior concave substantially spherical, or toric, surface and peripheral area. The multi-pane, multi-geometry eye-shield of this embodiment of the invention further comprises a cylindrical inner eye-shield member having an anterior convex surface and peripheral area and a posterior concave substantially cylindrical surface and peripheral area. This embodiment of the invention further comprises a substantially, or partially, posterior gasket member, the gasket member further comprising an outermost anterior, substantially spherical, peripheral surface adapted for interfacing to the concave spherical, or toric, posterior surface peripheral area of the spherical anterior outer eye-shield, the gasket member further comprising an inner anterior, substantially cylindrical, peripheral surface at least partially within the outermost anterior peripheral surface and adapted for interfacing to the posterior concave cylindrical surface peripheral area of the cylindrical inner eye-shield member. Preferably, the inner cylindrical anterior peripheral surface of this embodiment of the invention is recessed relative to the outermost anterior peripheral surface to allow a space between the inner and outer eye-shield members. The posterior gasket member of this embodiment of the invention is mostly, or substantially, posterior to both the spherical anterior outer eye-shield and the cylindrical inner eye-shield, but not an entire eye-shield apparatus including an eye-shield apparatus frame member.

However, it will be appreciated from the detailed description and figures hereof, that the gasket partially envelopes, encircles or encloses in a quasi- or semi-annular fashion, one or more of the eye-shield members adjacent their outer peripheral edges.

An exemplary gasket periphery shape is provided such that, similar to the gasket of the first embodiment of the invention (and other embodiments of the invention), though typically the gasket would not be perfectly circular, it does preferably have multiple curved peripheral edge portions forming the outline of an eye-shield periphery, such as in the case of a standard pair of goggles having an upper slightly curved brow portion, two semi-annular curved ends and two semi-annular curved lobe portions, one curved lobe portion beneath each area of the eye-shield adapted for being located directly in front of a user's eyes, the two semi-annular curved lobe portions being interconnected centrally by an inverted curved semi-annular portion adapted for being located directly over a user's nose. It will be appreciated that other peripheral shapes may be employed, whether curved or not curved, without departing from the true scope and spirit of the invention.

This aspect of the invention provides a fashionable goggle or eye-shield mask that is desirable and pleasing in appearance. The goggle or eye-shield mask is desirable because the spherical outer eye-shield provides a wearer protection from invasive matter to the eyes that is windblown or airborne, such as snow and ice, while still providing wearers a broad range of vision, a less distorted image, less glare, and an overall more comfortable and enjoyable experience. The goggle or eye-shield mask is fashionable and pleasing in appearance by today's standards because it provides for a currently in-fashion spherical outer lens that may be implemented with, for example, an "infinity-type" lens goggle where the spherical peripheral surface area of the lens material itself extends to the ultimate extent of the anterior perimeter surface of the goggle.

In accordance with another embodiment and according to a second aspect of the invention, there is provided a multi-pane, multi-geometry eye-shield as described in connection with each embodiment of the previously described, aspect of the invention, wherein the eye-shield is further adapted for heating. The device of this aspect of the invention further comprises heating of the eye-shield and assists in providing a goggle or eye-shield mask that is fog and condensation resistant, or dew resistant, by raising the temperature of the surface of the eye-shield above that temperature at which condensation forms. Limiting the formation of condensation, or fogging, on a lens provides a safer and more enjoyable environment and experience for a wearer.

Further in accordance with this second aspect of the invention, the eye-shield adapted for heating further preferably comprises a heater attached to at least one of the eye-shield members—preferably for purposes of this invention to the cylindrical eye-shield member. The device of this aspect of the invention of attaching a heater to one of the eye-shield members enables direct heating of the eye-shield. Directly heating the eye-shield additionally helps to effectively prevent fogging and condensation from forming on the eye-shield, creating a safer and more enjoyable environment for the wearer.

Still further in accordance with this second aspect of the invention of a heated multi-pane, multi-geometry eye-shield adapted for heating, with a heater attached to one of the eye-shields, preferably comprises a thin-film, electrically conductive heater preferably attached to the anterior convex surface of the cylindrical posterior inner eye-shield member, and a plurality of electrical contact members adapted for interconnecting the heater and a power source preferably on the eye-shield. The thin-film heater of this aspect of the invention may, for example, preferably be comprised of a thin-film transparent heater such as may be made with Indium Tin Oxide (ITO) or other currently available thin-film heating material.

The device of this aspect of the invention of attaching a thin-film heater preferably to the anterior convex surface of the cylindrical posterior eye-shield member, or cylindrical inner eye-shield member in accordance with the second embodiment of the invention, lowers manufacturing costs of a goggle or eye-shield that is currently fashionable, appealing to the eye and desirable to wear while still maintaining an ability to heat the eye-shield by supplying power through the electrical contact members to combat the problem of fog and condensation. Evenly depositing a thin-film layer on a spherical, or toric, member has not been developed or taught heretofore, and this in part accounts for what would be excessive and greater costs associated with attempting to do so. By attaching the thin film member to the posterior cylindrical eye-shield in accordance with the present invention, wearers benefit by having the capacity to heat the goggles or eye-shield mask comprising a currently more fashionable and appealing spherical lens while still maintaining lower development and manufacturing costs of the eye-shield apparatus.

Thus, in one embodiment of the second aspect of the invention, there is provided a multi-pane, multi-geometry eye-shield adapted for converting electrical power input into heating of the eye-shield, the eye-shield being adapted to be installed into a frame of a goggle or protective mask, comprising: a spherical anterior outer eye-shield member having an anterior convex substantially spherical, or toric, surface and peripheral area and a posterior concave substantially spherical, or toric, surface and peripheral area. The eye-shield in accordance with this embodiment of the invention further comprises: a cylindrical posterior inner eye-shield member having an anterior convex cylindrical surface and peripheral area and a posterior concave cylindrical surface and peripheral area, a heating member preferably attached to the anterior convex surface of the cylindrical posterior inner eye-shield member, a plurality of electrical contact members adapted for interconnecting the heating member and a power source, such as a battery comprised of a rechargeable lithium-ion battery, or other commonly available battery, wherein preferably the battery is carried on the frame or a strap of the goggle. This embodiment of the invention further comprises a multi-surface gasket member generally substantially interposed between the anterior and posterior eye-shield members forming a water-tight and air-tight space therebetween—the space being bounded by the semi- or quasi-annular gasket and the eye-shield members, comprising the eye-shield structure, and which are adjoined at or near the peripheral edges of each of the eye-shield members. Thus, the water-tight and air-tight space is formed between the anterior and posterior eye-shield members of the eye-shield structure and the gasket.

The gasket member of this embodiment of the invention comprises an anterior peripheral, substantially spherical, or toric, surface adapted for interfacing to the concave posterior spherical, or toric, surface peripheral area of the spherical anterior eye-shield member, and the gasket also comprises a posterior peripheral, substantially cylindrical surface adapted for interfacing to the convex cylindrical anterior surface peripheral area of the cylindrical posterior eye-shield member. Preferably, in accordance with this embodiment of the invention, the plurality of electrical contact members, or lead wires, of the multi-pane, multi-geometry eye-shield communicate through the gasket member without compromising the water-tight or air-tight semi-annular space.

In another embodiment of the second aspect of the invention, there is provided a multi-pane, multi-geometry eye-shield adapted for converting electrical power input into heating of the eye-shield, the eye-shield being adapted to be installed into a frame of a goggle or protective mask, comprising: a spherical anterior outer eye-shield member having an anterior convex substantially spherical, or toric, surface and peripheral area and a posterior concave substantially spherical, or toric, surface and peripheral area. The eye-shield in accordance with this embodiment of the invention further comprises: a cylindrical posterior inner eye-shield member having an anterior convex cylindrical surface and peripheral area and a posterior concave cylindrical surface and peripheral area, a heating member preferably attached to the anterior convex surface of the cylindrical posterior inner eye-shield member, a plurality of electrical contact members adapted for interconnecting the heating member and a power source, such as a battery comprised of a rechargeable lithium-ion battery, or other commonly available battery, wherein preferably the battery is carried on the frame or a strap of the goggle. This embodiment of the invention further comprises a multi-surface gasket member generally substantially located posterior of the anterior and posterior, also known as inner, eye-shield members, but created in an annular fashion with an inner recessed area so as to provide for holding the eye-shield members in an orientation such that a water-tight and air-tight space is created between the eye-shield members. That is, the space is bounded by the semi- or quasi-annular gasket and the eye-shield members, comprising the eye-shield structure, in that the eye-shield members are essentially adjoined, or sealed, at or near the peripheral edges of each of the eye-shield members. Thus, the water-tight and air-tight space is formed between the anterior and posterior eye-shield members of the eye-shield structure and the gasket.

The gasket member of this embodiment of the invention comprises an anterior peripheral, outermost substantially spherical, or toric, surface adapted for interfacing to the concave posterior spherical, or toric, surface peripheral area of the spherical anterior eye-shield member, and the gasket also comprises an anterior inner recessed peripheral, substantially cylindrical surface adapted for interfacing to the concave posterior cylindrical surface peripheral area of the cylindrical posterior (or inner) eye-shield member. Preferably, in accordance with this embodiment of the invention, the plurality of electrical contact members, or lead wires, of the multi-pane, multi-geometry eye-shield communicate through the gasket member without compromising the water-tight or air-tight space formed by the eye-shield members and the gasket. The posterior gasket member of this embodiment of the invention is mostly, or substantially, posterior to both the spherical anterior outer eye-shield and the cylindrical posterior, or inner, eye-shield, but not an entire eye-shield apparatus including an eye-shield apparatus frame member. However, it will be appreciated from the detailed description and figures hereof, that the gasket partially envelopes, encircles or encloses in a quasi- or semi-annular fashion, one or more of the eye-shield members adjacent their outer peripheral edges.

The device of these embodiments of the invention provide a fashionable and desirable goggle, or eye-shield mask, that is easy and cost effective to manufacture and which is also capable of being heated, as with a battery pack carried on the goggle frame, the goggle strap or the user's person or vehicle (such as a quad runner or a snowmobile). The spherical anterior eye-shield member provides wearers with a comfortable goggle or eye-shield mask that provides a wide range of vision, a clear image, little glare, and overall an improved wearing experience. Heating the eye-shield provides fog and condensation resistance. This functionality of the present invention enhances the visibility of the wearer and lends to a safer activity. Further, the provision of a water-tight and air-tight seal between the panes of the multi-pane, multi-geometry lens eye-shield further enhances the power efficiency and fog preventing capability of the eye-shield and thus lends to an improved overall eye-shield system.

Further, in accordance with another aspect of the invention, the eye-shield forms an air-tight and/or water-tight space between the panes of the multi-pane, multi-geometry eye-shield or lens, whether the eye-shield is adapted for heating or not. Further, in the case of a multi-pane, multi-geometry eye-shield adapted for heating, the plurality of electrical contact members of the eye-shield adapted for heating with a thin-film heater preferably communicate through the gasket member, and/or the circuits or wires leading up to the contact members communicate through the gasket member, without compromising the water-tight or air-tight space. The device of this aspect of the invention allows for a greater resistance to fog and condensation from forming on the eye-shield. The water-tight or air-tight semi-annular space provides the ability to keep moisture, and in turn condensation, from forming between multiple layers of the multi-pane eye-shield.

In accordance with yet another aspect of the invention, the multi-pane, multi-geometry eye-shield of the invention may be adapted for use in such protective eye-shield apparatus as a ski goggle, a military or tactical goggle, a paintballing mask or goggle, a helmet visor, and/or other commercial protective eye-shields or eye-wear.

The subject matter of the present invention is particularly pointed out and distinctly claimed in the concluding portion of this specification. However, both the organization and method of operation, together with further advantages and objects thereof, may best be understood by reference to the following descriptions taken in connection with accompanying drawings wherein like reference characters refer to like elements.

BRIEF DESCRIPTION OF THE DRAWINGS

FIG. 3a is a front perspective view of a first embodiment of a gasket in accordance with at least a portion of the invention;

FIG. 3b is a perspective view of the embodiment of the gasket of FIG. 3a;

FIG. 3c is a right-side perspective section view of the gasket of FIGS. 3a and 3b cut on a sagittal plane through a portion of the gasket adapted to be located directly above, and adjacent, a user's nose;

FIG. 3d is a right-side perspective section view of the gasket of FIGS. 3a and 3b, but cut on a different plane through a portion of the gasket adapted to be located over a user's left eye;

FIG. 3e is a bottom perspective section view of the gasket of FIGS. 3a and 3b cut on a horizontal plane cutting just above the bridge of the nose of the gasket;

FIG. 3f is a top perspective section view of the gasket of FIGS. 3a and 3b cut on a horizontal plane cutting just below the bridge of the nose of the gasket;

FIG. 3g is a rear perspective view of the gasket of FIGS. 3a and 3b;

FIG. 3h is a front perspective view of a second embodiment of a gasket in accordance with at least a portion of the invention;

FIG. 3i is a rear perspective view of the gasket of FIG. 3h;

FIG. 4b is a front perspective view of a goggle having installed thereon a multi-pane, multi-geometry eye-shield in accordance with an aspect of the invention;

FIG. 4c is a right-side perspective section view of the goggle of FIG. 4b cut on a plane through a portion of the gasket adapted to be located above, and adjacent, a user's nose;

FIG. 6a is a front perspective view of an embodiment of an anterior spherical, or toric, eye-shield;

FIG. 6b is a perspective view of the anterior spherical eye-shield of FIG. 6a;

FIG. 6c is a right-side perspective section view of the anterior spherical eye-shield of FIGS. 6a and 6b cut on a sagittal plane through a portion of the anterior spherical eye-shield adapted to be located directly above, and adjacent, a user's nose;

FIG. 6d is a right-side perspective section view of the anterior spherical eye-shield of FIGS. 6a and 6b, cut on a different plane than that of FIG. 6c, through a portion of the anterior spherical eye-shield adapted to be located over a user's left eye;

FIG. 7b is a perspective view of the cylindrical eye-shield of FIG. 7a;

FIG. 10b is a top perspective section view of the goggle of FIG. 10a;

FIG. 10c is a bottom perspective section view of the goggle of FIG. 10a;

FIG. 11a is a front perspective view of an embodiment of a gasket in accordance with at least a portion of the invention not adapted for heating;

FIG. 11b is a perspective view of the embodiment of the gasket of FIG. 11a;

FIG. 11c is a sectional right side perspective view of the gasket of FIGS. 11a and 11b cut on a sagittal plane through a portion of the gasket adapted to be located directly above, and adjacent, a user's nose;

FIG. 11d is a sectional right side perspective view of the gasket of FIGS. 11a and 11b, but cut on a different plane through a portion of the gasket adapted to be located directly over a user's left eye;

FIG. 11e is a sectional bottom perspective view of the gasket of FIGS. 11a and 11b cut on a horizontal plane just above the bridge of the nose of the gasket;

FIG. 11f is a sectional top perspective view of the gasket of FIGS. 11a and 11b cut on a horizontal plane just below the bridge of the nose of the gasket;

FIG. 12a is a front perspective view of a goggle in accordance with an embodiment of the invention, and FIG. 12b is a sectional right side perspective view of the goggle shown in FIG. 12a.

DETAILED DESCRIPTION OF THE INVENTION

First Embodiment

Figure 1A:
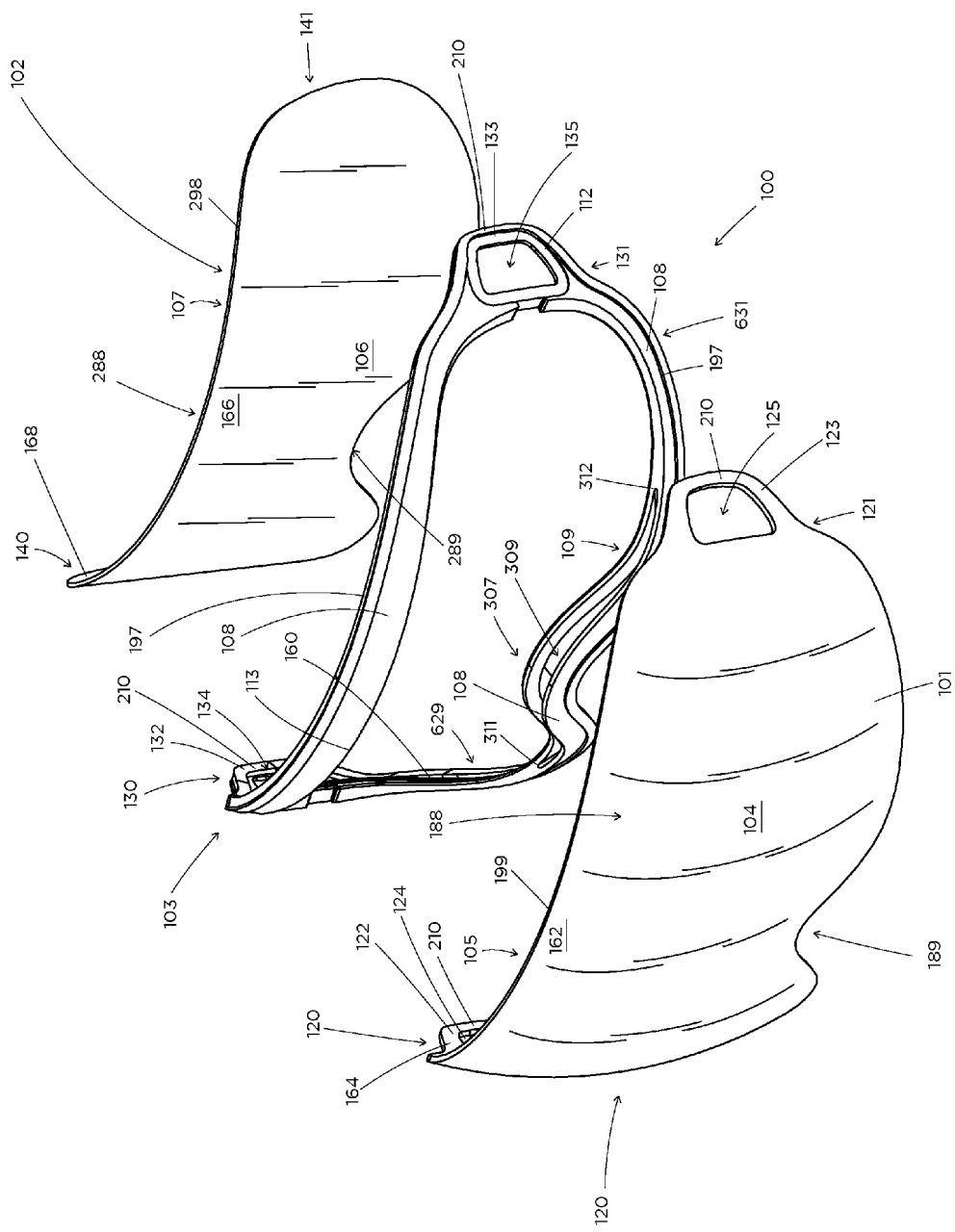
FIG. 1a is an exploded perspective view of a multi-pane, multi-geometry goggle eye-shield in accordance with an embodiment of at least a part of the invention.

Referring to FIGS. 1a, 2a, 3a-g, 5a, 6a-d, and 7a-d, there are shown multi-pane, multi-geometry eye-shield components for an embodiment of a multi-pane, multi-geometry eye-shield 100, such as may be adapted for use in a ski goggle, that comprises an outer spherical, or toric, anterior eye-shield member 101 preferably made of a suitable optical grade plastic that is transparent and translucent, such as polycarbonate plastic, and may be either machined or made by injection molding. The outer eye-shield member 101 has an anterior convex substantially spherical surface area 104, an anterior convex substantially spherical peripheral surface area 162, a posterior concave substantially spherical surface area 105, and a posterior concave substantially spherical peripheral surface area 164. The outer eye-shield member 101 has two ends 120, 121. On each end 120, 121 of outer eye-shield member 101, there is a hole 124, 125, each hole formed, or defined, by a loop or band 122, 123 of resilient, semi-rigid lens material at or near each end of lens 101, each hole and band serving as a portion of an interconnection mechanism 126, 127. The anterior eye-shield member 101 has an upper portion 188 and a lower nose-bridge portion 189.

The eye-shield 100 further comprises an inner cylindrical posterior eye-shield member 102 that is preferably made of a suitable optical grade plastic that is transparent and translucent, such as polycarbonate plastic, and may be either machined or made by injection molding. Inner cylindrical posterior eye-shield member 102 has an anterior convex substantially cylindrical surface area 106, an anterior convex substantially cylindrical peripheral surface area 166, a posterior concave substantially cylindrical surface area 107, and a posterior concave substantially cylindrical peripheral surface area 168. Cylindrical posterior inner eye-shield member 102 further comprises ends 140, 141, a peripheral edge 298, an upper portion 288 and a lower nose-bridge portion 289.

The eye-shield 100 further comprises a gasket member 103, preferably made of plastic, silicone, or other resilient material, part of which is interposed between the anterior spherical eye-shield member 101 and posterior cylindrical eye-shield member 102, such that when assembled there is formed a water-tight and air-tight space 450 between the gasket, the spherical eye-shield member and the cylindrical eye-shield member as seen in FIG. 4c. As shown for example in the exploded view of FIG. 1a, the gasket member 103 is shown interposed between the two eye-shield members 101, 102, but since the gasket member is an irregular shaped ring-like member (generally shown in the shape of the periphery of a goggle eye-shield), the gasket is actually only partially interposed between eye-shield members, that is at their peripheral areas. Thus, the gasket member 103 is said to create the space 450 between the eye-shield members 101, 102. The gasket member 103 has an anterior peripheral surface 108 shaped so as to be adapted for interfacing to the concave posterior surface peripheral area 164 of the spherical anterior eye-shield member 101, preferably such that the interface between the concave posterior surface area 164 and the anterior peripheral surface 108 form a water-tight and air-tight seal 451 as seen in FIG. 4c, around the perimeter edges of surfaces 164 and 108.

The gasket member 103 also has a posterior peripheral surface 109 adapted for interfacing to the convex anterior surface peripheral area 166 of the cylindrical posterior eye-shield member 102, preferably such that the interface between the convex anterior surface peripheral area 166 and the posterior peripheral surface 109 form a water-tight and air-tight seal 452 as seen in FIG. 4c, around the perimeter surface areas 166 and 109 of cylindrical eye-shield member 102 and gasket 103, respectively. On the posterior surface 109 is a ridge member 160 that is adapted such that it holds the cylindrical eye-shield member 102 firmly and securely against the posterior surface 109. On each side, or each end 130, 131, of gasket member 103, there is a hole 134, 135 each formed by a loop or band 132, 133 of resilient, semi-rigid gasket material at or near the end of gasket member 103, serving as a portion of an interconnection mechanism 126, 127.

The gasket member 103 is of an irregular shape to accommodate the spherical, or toric, shape of eye-shield member 101 on the anterior, or front, side of the eye-shield 100, and the cylindrical shape of the eye-shield member 102 on the posterior, or rear, side of the eye-shield. These shapes and shaping of the gasket member 103 are particularly concerned with interfacing to the peripheral shaping of the peripheral surface areas, posterior peripheral surface area 164 of anterior eye-shield member 101, and anterior peripheral surface area 166 of posterior eye-shield member 102, since these are the peripheral areas that mate with corresponding surfaces 108, 109, respectively, of the gasket member to preferably form an air-tight, water-tight seal between the three members. Accordingly, the posterior peripheral surface area 164 of anterior eye-shield member 101 mates with anterior peripheral surface area 108 of the gasket member 103 to form an air-tight, water-tight seal, and anterior peripheral surface area 166 of posterior eye-shield member 102 mates with posterior peripheral surface area 109 of the gasket member 103 to likewise form an air-tight, water-tight seal. As may be seen in FIGS. 1a, 3b-3f and 4c, the normal distance between the peripheral surfaces 108 and 109 of the gasket 103 varies along the peripheral length of the gasket to accommodate the shape variation in the eye-shield members 101 (spherical-, or toric-shaped), 102 (cylindrical-shaped). As shown in FIGS. 3e and 3f, the normal distance between these peripheral surfaces 108, 109 is at a minimum near the uppermost portion 305 of the gasket (and hence eye-shield 100) as well as ends 130, 131 of the gasket and just around the lower outer corners 629, 631 of the gasket. At the bridge-of-the-nose portion 307 of the gasket 103, the normal distance is greatest between these peripheral surfaces 108, 109, as evidenced by channel 309 which is at its widest directly over the bridge of the nose and which tapers in width as the channel extends to locations 311, 312 where the channel no longer exists. Thus, as the channel 309 gradually narrows as it extends away from the sagittal centerline of the gasket in each direction to the ends 130, 131 of the gasket to and beyond locations 311, 312 to be more closely adjacent and in front of a position adapted to be in front of a user's eyes at 311, 312, where the channel narrows to a point.

The gasket 103 has an anterior peripheral lip 197 around the anterior periphery of the gasket within which in one embodiment of the invention the outermost peripheral edge 199 of the eye-shield member 101 rests, while the foregoing lip 197 aids in retaining the corresponding composite eye-shield member 101. It will be appreciated that at least as to an "infinity-type" lens anterior eye-shield member 101, where the eye-shield member extends to the full extent of the outer eye-shield, lip 197 would not be desirable or necessary.

Figure 5A:
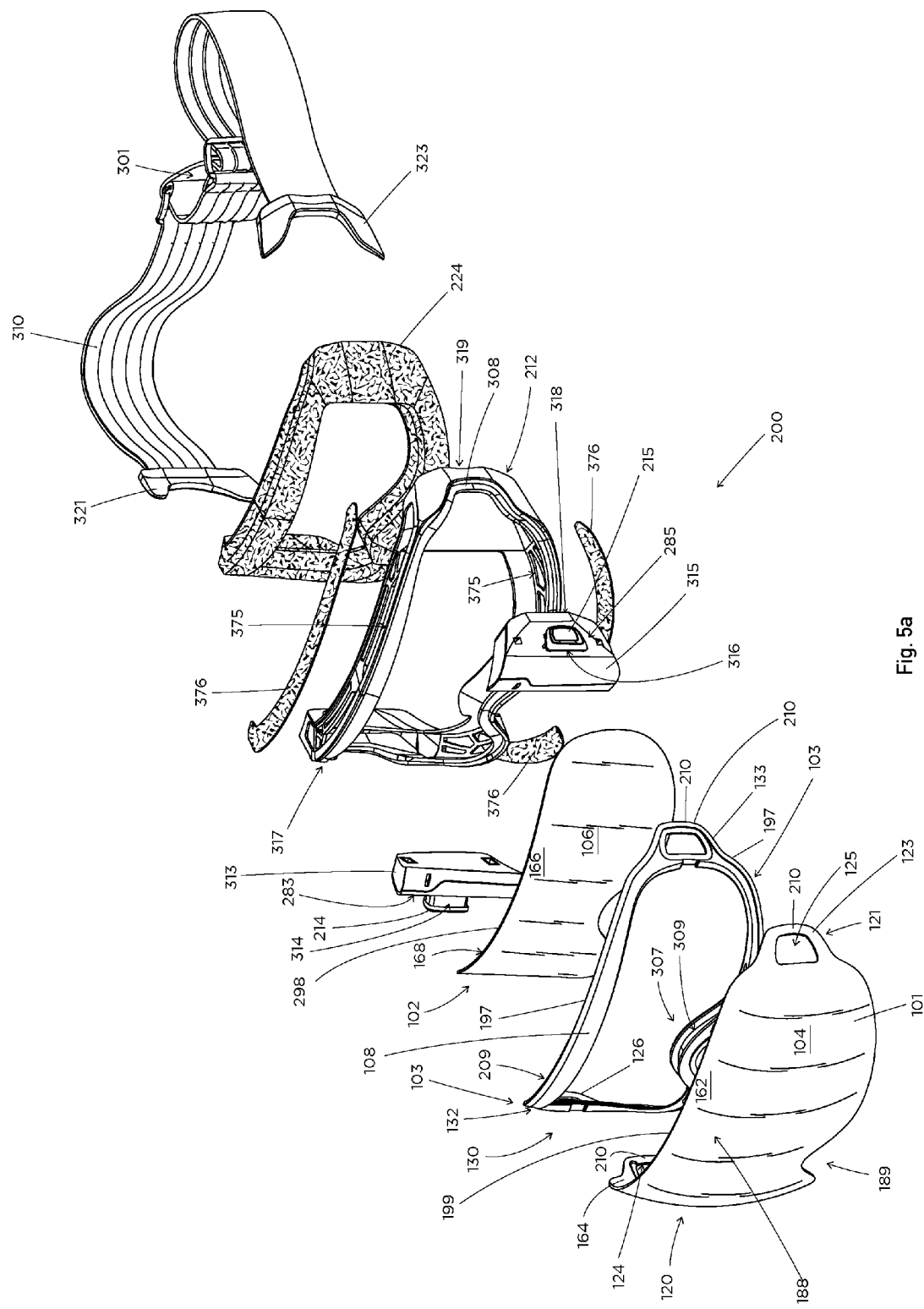
FIG. 5a is an exploded perspective view of an embodiment of the invention not adapted for heating and as implemented in a multi-pane, multi-geometry goggle eye-shield.

The loops or bands 132, 133 may comprise an insert material, for example of higher-durometer plastic, that serves to enhance the strength, wear and fit characteristics of the loop band material around a post portion 214, 215 of a goggle frame 212 (see FIG. 5a).

Referring now additionally to FIG. 5a, there is shown a goggle 200 comprising a multi-pane, multi-geometry goggle eye-shield 100 in accordance with the first embodiment of the invention. The goggle 200 is comprised of an anterior spherical lens 101, a translational gasket member 103 and a posterior cylindrical lens 102, all preferably made of a suitable optical grade plastic that is transparent and translucent, such as polycarbonate plastic, and may be either machined or made by injection molding, as described previously.

The translational gasket member 103 preferably comprises an anterior peripheral surface, or interface portion, 108 and a posterior peripheral surface, or interface portion, 109. The anterior peripheral surface 108 is shaped so as to be adapted to receive a posterior peripheral surface area 164 of the spherical outer lens 101, and the posterior peripheral surface 109 is shaped so as to be adapted to receive an anterior peripheral surface area 166 of the cylindrical inner lens 102. The gasket member 103 further comprises a posterior peripheral area, structure or lip 209 that resides in a channel, or groove portion 308 of a frame or body member 212 of the goggle 200.

Loop/band interconnection mechanism 122, 123, 132, 133, preferably further comprises an extent portion 210 at the furthest extent of the loop/band to facilitate easy grabbing, installation and removal of the loop/band interconnection mechanism from the goggle frame 212. Preferably the loop/band interconnection mechanism portions 122, 123, 132, 133, comprises an integral extension of the same material forming the lens 101 and gasket member 103, which optionally may be formed in laminate fashion together with the inner lens 102 as well. It will be appreciated that the inner lens 102 may or may not have such a loop/band interconnection mechanism portion.

Similar to the alternate embodiment shown and described hereafter in connection with FIGS. 4a, 9a-9b, 10b, 11b-11g and 12b, the gasket member 103, goggle frame 212, and loop/band interconnection mechanism portions 132, 133, corresponding to gasket 103", goggle frame 212" and loop/band interconnection mechanism portions 132", 133" described hereafter, may further optionally comprise a plurality of spring snap members 407 which may be integrally formed with the gasket member and positioned at multiple locations around the posterior periphery of the gasket member. Corresponding to each spring snap member 407, there may be provided a receptacle 409 (see FIG. 4a), wherein each receptacle would be located at a corresponding location around the anterior periphery of the goggle frame 212, each receptacle in such an alternate embodiment being adapted for receipt and retention, by containing and spring force retention of each spring snap member on a catch portion 411 of each receptacle, so as to be adapted to securely retain the eye-shield 100 on the goggle frame 212. These optional spring snap members 407 and receptacles 409 may be optionally provided to enable a user to position and securely retain the eye-shield member 100 on the goggle frame 212 in one embodiment, so as to allow easy installation and removal of the eye-shield from the goggle frame, while at the same time allowing interconnection of the eye-shield 100 with the posts 214, 215 of the goggle frame 212, such that the loops/bands comprising interconnection mechanism 122, 123, 132, 133, 126, 127 serve to help reinforce attachment of the eye-shield 100 to the goggle frame 212 as may be necessary. It will be appreciated that other apparatus for interconnecting the eye-shields of the invention to the goggle body, or frame, would not necessarily depart from the true scope and spirit of the invention as claimed.

Loop/band interconnection mechanism 122, 123, 132, 133, 126, 127 further comprises the extent portion 210 at the furthest extent of the loop/band to facilitate easy grabbing, installation and removal of the loop/band interconnection mechanism from the goggle frame 212. Preferably the loop/band interconnection mechanism 122, 123, 132, 133, 126, 127 comprises an integral extension of the same material forming the lens 101 and gasket member 103, formed in laminate fashion together. It will be appreciated that the inner lens 102 may or may not have such a loop/band interconnection mechanism portion.

Second Embodiment

Referring to FIGS. 1b, 2b, 3h-3i, 5b, 6a-d, 7e-f and 10a-10c, in a second embodiment of the invention, there is provided a multi-pane, multi-geometry goggle eye-shield 100' adapted for heating with a power source, such as for example a lithium-ion battery 229, carried for example on a goggle frame, a goggle strap, another eye-shield frame or on a user's person. Just as with the eye-shield 100, the eye-shield 100' also comprises a spherical, or toric, anterior outer eye-shield member 101 preferably made of a suitable optical grade plastic that is transparent and translucent, such as polycarbonate plastic. Eye-shield member 101 may be either machined or made by injection molding and has an anterior convex substantially spherical surface area 104 and a substantially spherical anterior peripheral surface area 162. The eye-shield member 101 further comprises a posterior concave substantially spherical surface area 105 and a posterior substantially spherical peripheral surface area 164. On each side or end 120, 121 of outer eye-shield member 101, there is a hole 124, 125, each hole formed by a loop or band 122, 123 of resilient, semi-rigid lens material at or near the end of the eye-shield, or lens, 101, serving as a portion of an interconnection mechanism 126, 127.

Similar to the eye-shield 100 of the first embodiment of the invention, the eye-shield 100' of the second embodiment of the invention further comprises a cylindrical posterior inner eye-shield member 102' preferably made of a suitable optical grade plastic that is transparent and translucent, such as polycarbonate plastic. Inner eye-shield member 102' may be either machined or made by injection molding and has an anterior convex cylindrical surface area 106' and an anterior convex cylindrical peripheral surface area 166'. Inner eye-shield member 102' further comprises a posterior concave cylindrical surface area 107' and a posterior concave cylindrical peripheral surface area 168'. Cylindrical posterior inner eye-shield member 102' further comprises ends 140', 141', a peripheral edge 298', an upper portion 288' and a lower nose-bridge portion 289'.

Unlike inner eye-shield member 102, preferably attached to the anterior convex surface 106' of the cylindrical posterior inner eye-shield member 102', there is a thin-film, electrically conductive heater 114, preferably made of a translucent, conductive material, such as Indium Tin Oxide (ITO). The conductive heater 114 is preferably applied by a process, such as where an ITO-coated polyester film is adhered to a polycarbonate lens with an optically clear adhesive, or where ITO is applied directly onto a polycarbonate lens by ion sputtering. In either case, only a very thin and uniform thickness of ITO (on the order of 800 angstroms, or 80 nanometers, thick) across the surface 106' is required. Of course, it will be appreciated by those of ordinary skill in the art that other available translucent, conductive heater materials may be used without departing from the true scope and spirit of the invention.

The cylindrical posterior inner eye-shield member 102' additionally has a plurality of electrical contact members 115, 116 made from an electrically conductive material, located preferably near the perimeter and near the ends 140', 141' of eye-shield member 102', and on the anterior surface 106' of the inner eye-shield member 102'. Electrical contact members 115, 116 are adapted for interconnecting the heating member 114 and a power source 229. Interconnecting the electrical contact members 115, 116 with the thin film heater 114, there are provided a plurality of bus bars 501, 502 included on the upper and lower portions 288', 289', respectively of cylindrical inner eye-shield member 102'. In greater detail, contact members 115, 116 comprise a hole on the eye-shield 102' and a contact rivet, in essence, as part of the remainder of the contact or circuit (e.g., contacts 112, 113, or contacts 112', 113').

The goggle eye-shield 100' further comprises a gasket member 103', preferably made of plastic, silicone, or another resilient material, interposed between the anterior spherical eye-shield member 101 and the posterior cylindrical eye-shield member 102'. When assembled, the gasket member 103', anterior spherical eye-shield member 101 and posterior cylindrical eye-shield member 102' define and form a water-tight and air-tight semi-annular space 450' therebetween as illustrated in FIG. 4c. The gasket member 103' has an anterior peripheral surface 108' shaped so as to be adapted to interface to the concave posterior peripheral surface area 164 of the spherical anterior eye-shield member 101, preferably such that the interface between the concave posterior surface area 164 and the anterior peripheral surface 108' form a water-tight and air-tight seal 451' spherical peripheral as seen in FIG. 4c, around the perimeter edges of surfaces 164 and 108'.

The gasket member 103' also has a posterior peripheral cylindrical surface 109' adapted for interfacing to the convex anterior cylindrical peripheral surface area 166' of the cylindrical posterior eye-shield member 102'. Preferably the convex anterior cylindrical peripheral surface area 166' and the posterior cylindrical surface peripheral area 109' interface to form a water-tight and air-tight seal 452' as seen in FIG. 4c, adjacent the perimeter edges of surfaces 166' and 109'. Adjacent and substantially perpendicular to the posterior peripheral surface 109' there is a ridge member 160' that is adapted to help hold the cylindrical eye-shield member 102' firmly and securely against the posterior surface 109'. Adhesive (not shown) may be used to help establish the aforementioned air-tight and water-tight seals. On each end 130', 131' of gasket member 103', there is a hole 134', 135' each formed by a loop or band 132', 133' of resilient, semi-rigid gasket material at or near the end of gasket member 103', serving as a portion of an interconnection mechanism 126, 127.

The gasket member 103' also has a plurality of contact members 110, 111 made of electrically conductive material, at either end 130', 131' of the gasket 103' contact member 110, 111 attached preferably, to the loops/bands 132', 133', respectively, and are adapted for interconnecting the heating member 114 and the power source 229. In accordance with one embodiment of the invention, loops/bands 132', 133' further comprise metal contact rings 112, 113 that are contiguous with contact members 110, 111, respectively, and are molded, embedded, or deposited onto loops/bands 132', 133'. In such case, the contact rings 112, 113 would serve as part of interconnection mechanism 126, 127 in that they would interconnect the eye-shield 101' with an eye-shield apparatus frame, such as a goggle frame 212', and would also serve to interconnect the heating member 114 and the power source 229.

Figure 1B:
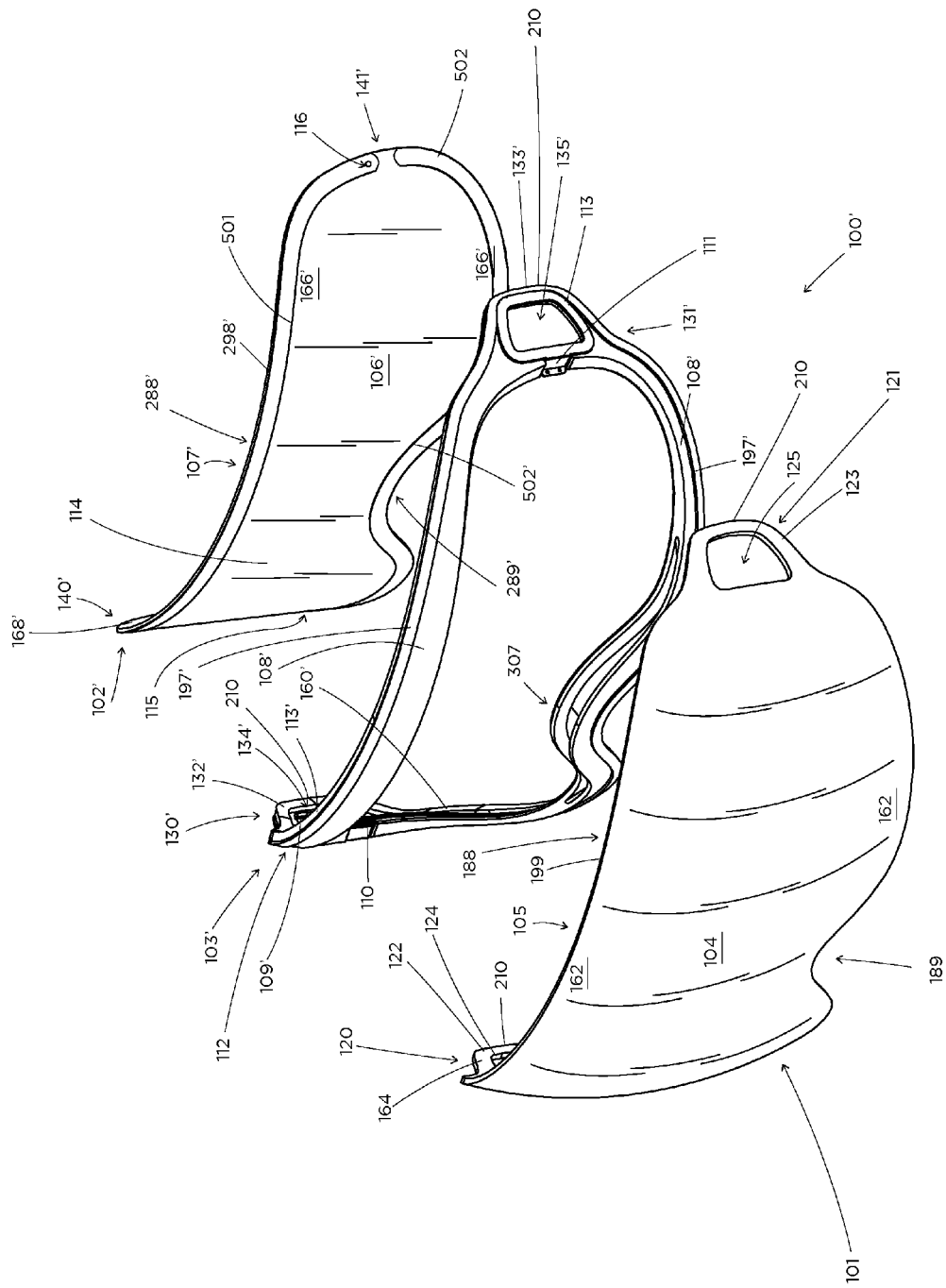
FIG. 1b is an exploded perspective view of an embodiment of a multi-pane, multi-geometry goggle eye-shield adapted for converting electrical power input into heating of the eye-shield in accordance with an embodiment of at least a part of the invention.
Figure 2A:
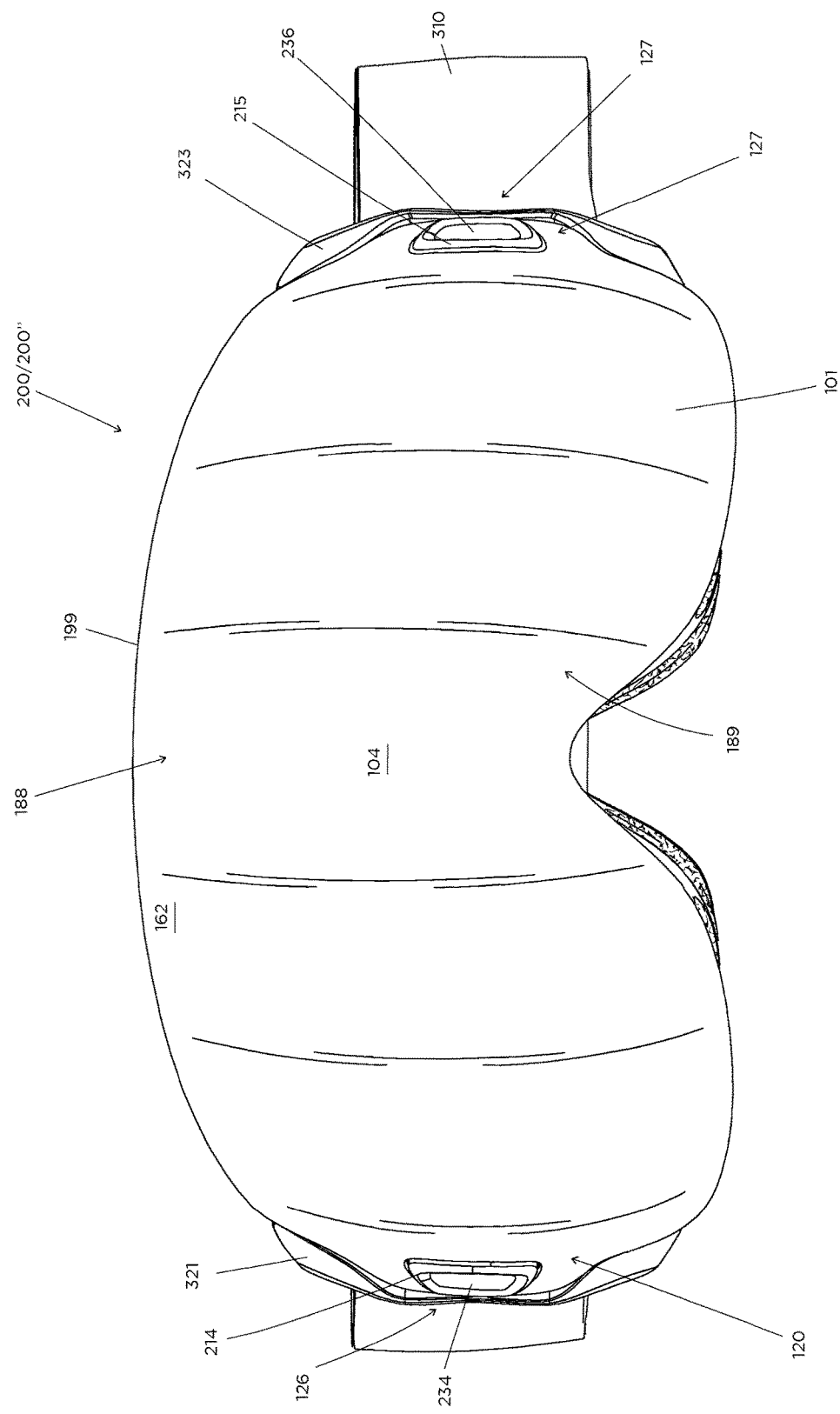
FIG. 2a is a front perspective view of an embodiment of a multi-pane, multi-geometry eye-shield on a ski goggle.
Figure 2B:
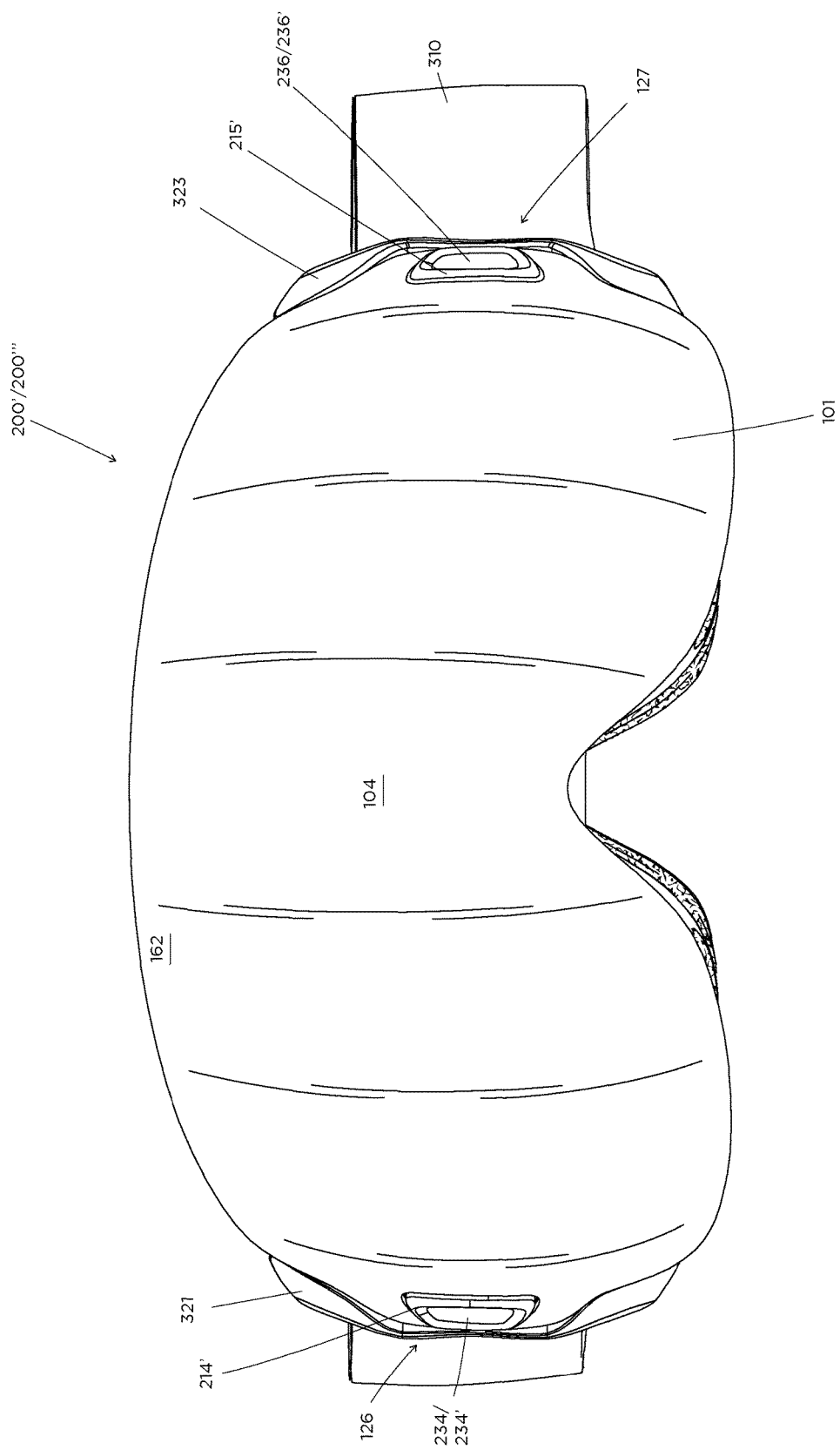
FIG. 2b is a front perspective view of another embodiment of a multi-pane, multi-geometry eye-shield on a ski goggle.

As shown for example in the exploded view of FIG. 1b, the gasket member 103' is shown interposed between the two eye-shield members 101, 102', but since the gasket member is an irregular shaped ring-like member (in the general shape of the periphery of a goggle eye-shield), the gasket is actually only partially interposed between eye-shield members, that is at their peripheral areas, and the gasket may also extend beyond the eye-shield members as shown. Thus, the gasket member 103' is said to create the space 450' between the eye-shield members 101, 102'. The gasket member 103' further comprises a posterior peripheral area, structure or lip 209' that resides in a channel, or groove portion 308' of a frame or body member 212' of the goggle 200'.

Alternatively, similar to that described in connection with the first embodiment above and fourth embodiment below in connection with FIGS. 4a, 9a-9b, 10b, 11b-11g and 12b, a plurality of spring snap members 407 and receptacles 409 may be employed to further secure interconnection of the eye-shield member 100' to the goggle frame member 212'.

Third Embodiment

Referring to FIGS. 2a, 6a-d, 7a-d, 8a, 9a, 11a-g and 12a-b there are shown multi-pane, multi-geometry eye-shield components for another, third, embodiment of a multi-pane, multi-geometry eye-shield 100", such as may be adapted for use in a ski goggle. As with eye-shields 100 and 100', eye-shield 100" (see FIG. 9a) comprises an outer spherical, or toric, anterior eye-shield member 101 preferably made of a suitable optical grade plastic that is transparent and translucent, such as polycarbonate plastic, and may be either machined or made by injection molding. The outer eye-shield member 101 has an anterior convex substantially spherical surface area 104, an anterior convex substantially spherical peripheral surface area 162, a posterior concave substantially spherical surface area 105, and a posterior concave substantially spherical peripheral surface area 164. The outer eye-shield member 101 has two ends 120, 121. On each end 120, 121 of outer eye-shield member 101, there is a hole 124, 125, each hole formed, or defined, by a loop or band 122, 123 of resilient, semi-rigid lens material at or near each end of lens 101, each hole and band serving as a portion of an interconnection mechanism 126, 127. The anterior eye-shield member 101 has an upper portion 188 and a lower nose-bridge portion 189.

The eye-shield 100" further comprises an inner cylindrical posterior eye-shield member 102 that is preferably made of a suitable optical grade plastic that is transparent and translucent, such as polycarbonate plastic, and may be either machined or made by injection molding. Inner cylindrical posterior eye-shield member 102 has an anterior convex substantially cylindrical surface area 106, an anterior convex substantially cylindrical peripheral surface area 166, a posterior concave substantially cylindrical surface area 107, and a posterior concave substantially cylindrical peripheral surface area 168. Cylindrical posterior inner eye-shield member 102 further comprises ends 140, 141, a peripheral edge 298, an upper portion 288 and a lower nose-bridge portion 289.

Figure 8A:
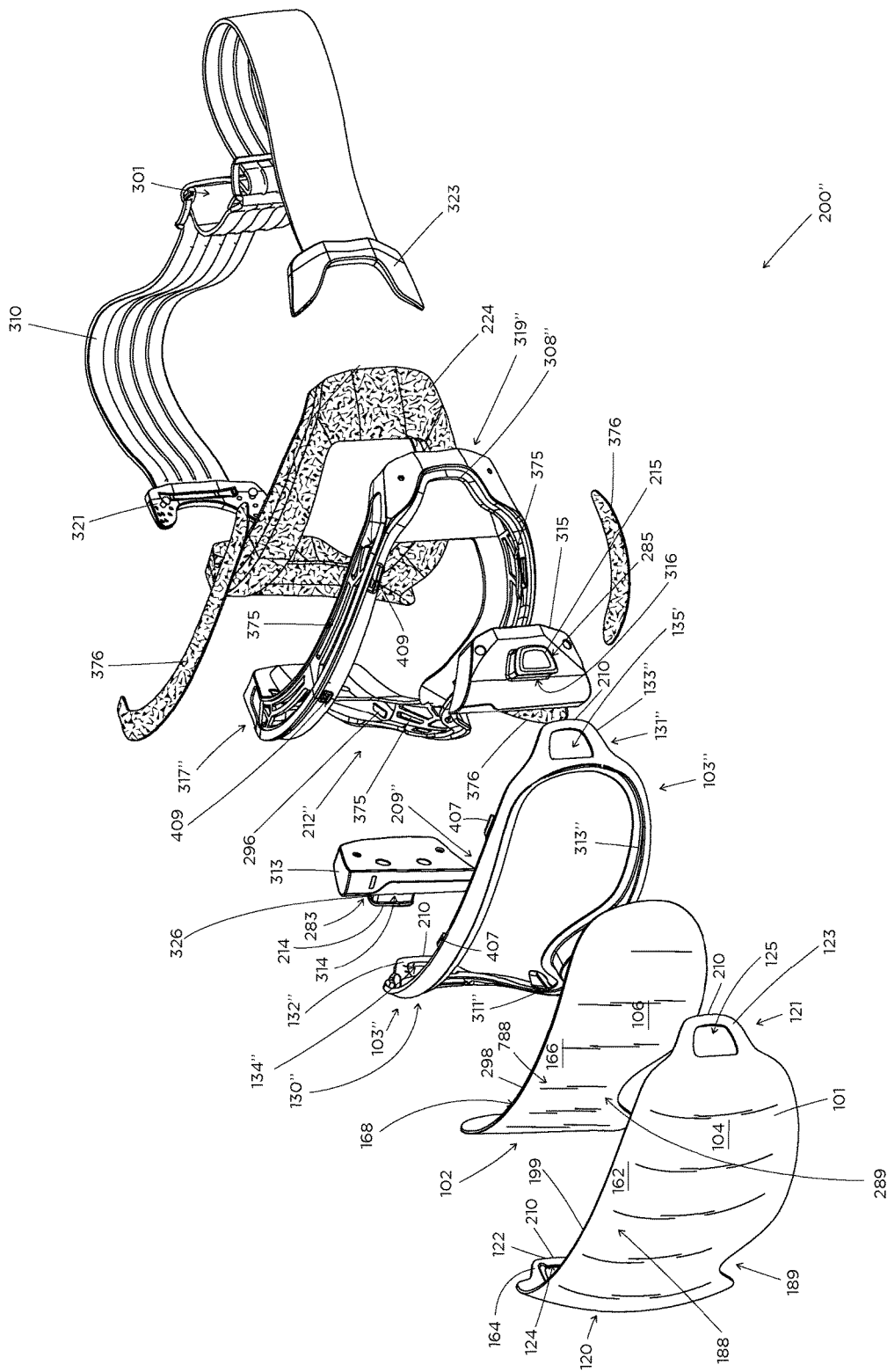
FIG. 8a is an exploded perspective view of an alternate embodiment of the invention not adapted for heating and implemented in a multi-pane, multi-geometry goggle eye-shield.

The eye-shield 100" further comprises a gasket member 103", preferably made of plastic, silicone, or other resilient material. Unlike gasket member 103 and 103', though gasket member 103" is considered to be located largely, or mostly, posterior to both anterior spherical eye-shield member 101 and posterior/interior cylindrical eye-shield member 102, the gasket nevertheless is also partially co-extensive in location with the eye-shield members in that it surrounds the periphery of at least eye-shield member 102. Nevertheless, especially as shown in FIG. 8a, the gasket is said to be located between the posterior/interior eye-shield member 102 and a goggle frame 212", in part because that is the manner in which it is constructed. In actuality, in the installed condition, the eye-shield member 101 resides on the anterior surface 108" of the gasket member 103", while the inner eye-shield member 102 reside somewhat within the gasket member 103" in that the peripheral edge portion 298 of the inner eye-shield member 102 resides within a recessed portion (at surface 109") of the gasket member. But in terms of general order of presentation, the most anterior eye-shield portion comprises eye-shield member 101, the next most posterior eye-shield portion comprises eye-shield member 102, and at least insofar as contact with goggle frame is concerned, the most posterior portion of the eye-shield 100" comprises the gasket member 103". Thus, as shown in the figures, the gasket member 103" encompasses in a quasi-annular fashion the peripheral edge of the eye-shield members 102. Accordingly, the gasket 103" preferably encompasses the entire peripheral edge portion 298 of the inner eye-shield member 102, so that the gasket comprises an entire unbroken ring. The eye-shield member 101 resides in a peripheral lip, as with peripheral lip 197 for the first embodiment of the invention, or it may comprise an infinity-type lens. Similar to previous embodiments, when assembled, eye-shield members 101, 102 and 103" form a water-tight and air-tight space 450" therebetween as seen in FIG. 12b. The gasket member 103" has an anterior peripheral surface 108" shaped so as to be adapted for interfacing to the concave posterior surface peripheral area 164 of the spherical anterior eye-shield member 101, preferably such that the interface between the concave posterior peripheral surface area 164 and the anterior peripheral surface 108" form a water-tight and air-tight seal 451" as seen in FIG. 12b, around the perimeter edges of adjacent surfaces 164 and 108".

The gasket member 103" also has an inner anterior peripheral surface 109" adapted for interfacing to the concave posterior peripheral surface area 168 of the cylindrical posterior/interior eye-shield member 102, preferably such that the interface between the concave posterior surface peripheral area 168 and the inner anterior peripheral surface 109" form a water-tight and air-tight seal 452" as seen in FIG. 12b, around the perimeter surface areas 168 and 109" of cylindrical eye-shield member 102 and gasket 103", respectively. On the inner anterior surface 109" is a recessed ridge 161 that holds the cylindrical eye-shield member 102 within the gasket 103" against inner anterior surface 109". The inner eye-shield member 102 nests within the inner ledge 309" at a location where the ledge 309" and the inner peripheral surface 109" meet and come together at a substantially 90 degree angle. On each side, or each end 130", 131", of gasket member 103", there is a hole 134", 135" each formed by a loop or band 132", 133" of resilient, semi-rigid gasket material at or near the end of gasket member 103", serving as a portion of an interconnection mechanism 126, 127.

The gasket member 103" is of an irregular shape to accommodate both the spherical, or toric, shape of the posterior peripheral surface area 164 of eye-shield member 101 on the outer anterior, or front, peripheral surface area 108" of the eye-shield 100", and the cylindrical shape of the posterior peripheral surface area 168 of the eye-shield member 102 on the inner anterior surface 109" of the gasket member 103". These shapes and shaping of the gasket member 103" are particularly concerned with the peripheral shaping of the peripheral surface areas, posterior peripheral surface area 164 of outer/anterior eye-shield member 101, and posterior peripheral surface area 168 of inner/posterior eye-shield member 102, since these are the peripheral areas that mate with corresponding surfaces 108", 109", respectively, of the gasket member to preferably form an air-tight, water-tight seal between the three members as shown at 451" and 452" of FIG. 12*b*.

As may be seen in FIGS. 11*b*-11*f* and 12*b*, the distance between the peripheral surfaces 108" and 109" of the gasket 103" varies along the peripheral length of the gasket to accommodate the shape variation in the eye-shield members 101 (spherical, or toric-shaped), 102 (cylindrical-shaped). As shown in FIGS. 11*e* and 11*f*, the normal distance between these peripheral surfaces 108", 109" is at a minimum near the uppermost portion 305" of the gasket (and hence eye-shield 100") as well as ends 130", 131" of the gasket. At the bridge-of-the-nose portion 307" of the gasket 103", the normal distance is greatest between these peripheral surfaces 108", 109", as evidenced by channel, or more accurately ledge 309" (as seen in FIGS. 11*c* and 11*d*). Accordingly, ledge 309" is at its widest directly over the bridge-of-the-nose portion 307" and it tapers in width as the ledge 309" extends to locations 311", 312" where the ledge is more narrow as extends around the ends 130", 131" and along the upper portion 305" of the gasket. Thus, as the ledge 309" extends away from the sagittal centerline of the gasket 103" in each direction to the ends 130", 131" of the gasket to and beyond locations 311", 312" to be more closely adjacent and in front of a position adapted to be in front of a user's eyes at 311", 312", the ledge tapers to a point (at 311", 312").

Unlike the gasket 103, the gasket 103" has no anterior peripheral lip around the anterior periphery of the gasket within which the outermost peripheral edge 199 of the eye-shield member 101 rests. This is because with this third embodiment of the eye-shield 100", the most anterior eye-shield member 101 is an infinity-type lens/eye-shield member 101 which extends to the ultimate foremost peripheral edge of the gasket 103". The peripherally extending gasket 103" which partially wraps around the outermost peripheral edge 199 of the eye-shield member 102 serves as a quasi-annular retaining member for holding the eye-shield member 102, whereas the eye-shield member 101 may be adhered to the surface 108" of the gasket with adhesive as for example with an adhesive backed thin gasket (not shown). The gasket member 103" further comprises a posterior peripheral area, structure or lip 209" that resides in a channel, or groove portion 308" of a frame or body member 212" of the goggle 200".

The loops or bands 132", 133" may comprise an insert material, such as a higher-durometer plastic material, or as with metallization, that serves to enhance the strength, wear, contact and fit characteristics of the loop band material around the post portions 214, 215 of a goggle frame 212" (see FIG. 8*a*).

Figure 9A:
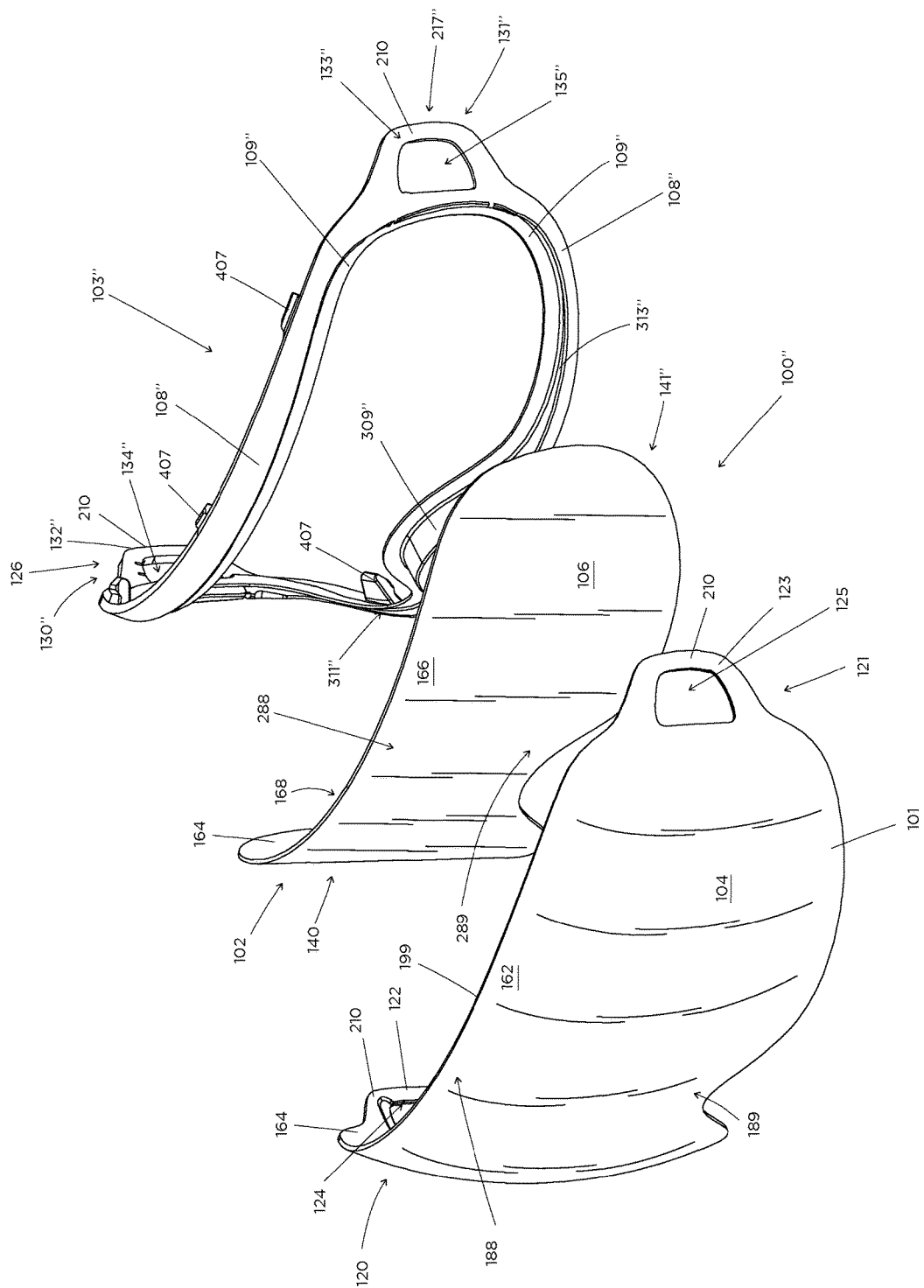
FIG. 9a is an exploded perspective view of a multi-pane, multi-geometry goggle eye-shield in accordance with an alternate embodiment of at least a part of the invention not adapted for heating.
Figure 9B:
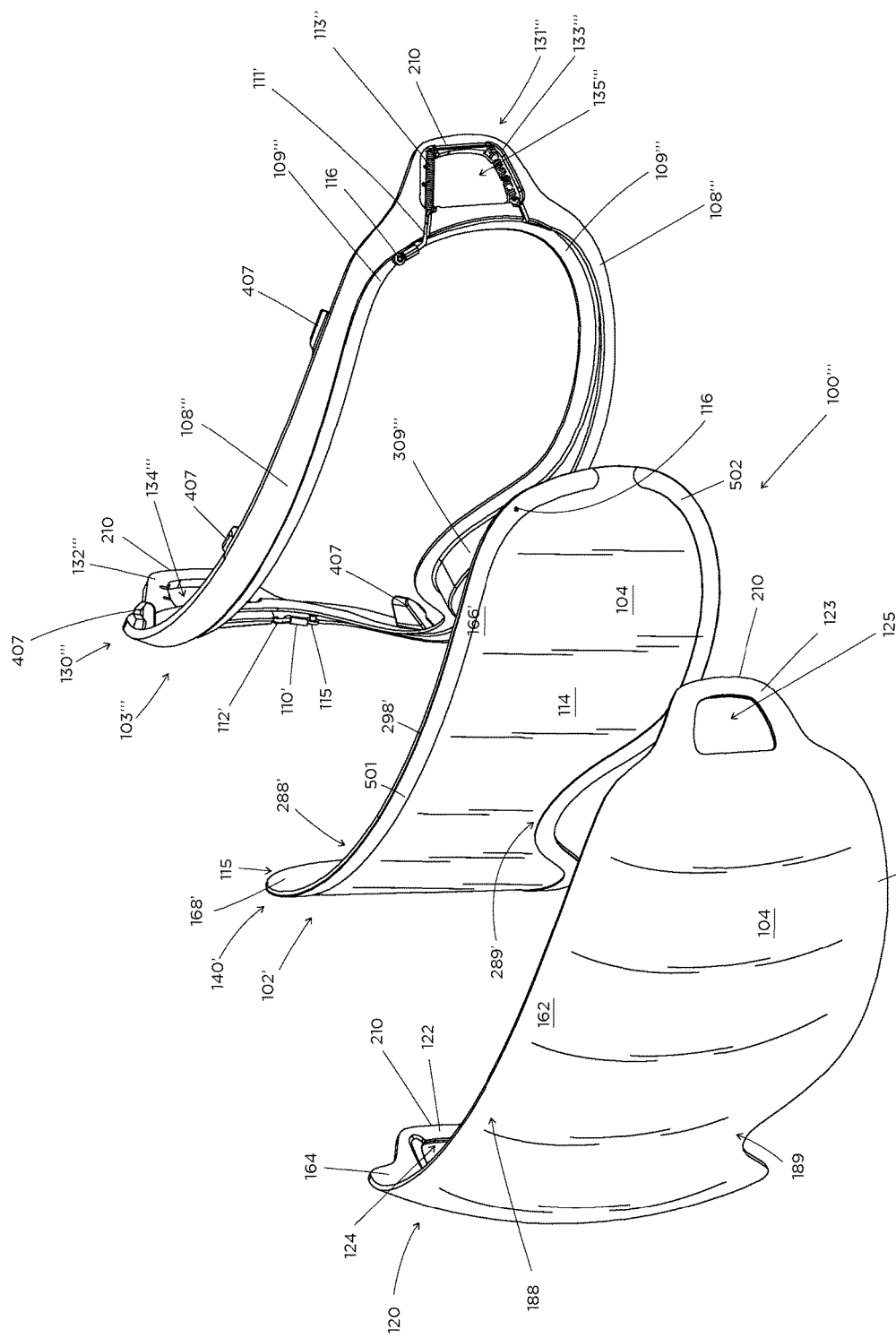
FIG. 9b is an exploded perspective view of a multi-pane, multi-geometry goggle eye-shield in accordance with another alternate embodiment of at least a part of the invention and adapted for converting electrical power input into heating of the eye-shield.

Referring now additionally to FIG. 8*a*, there is shown a goggle 200" comprising a multi-pane, multi-geometry goggle eye-shield 100" as shown in FIG. 9*a*) in accordance with the third embodiment of the invention. The goggle 200" is comprised of the anterior spherical lens 101, the inner/posterior cylindrical lens 102, and the gasket member 103", all preferably made of a suitable optical grade plastic that is transparent and translucent, such as polycarbonate plastic, and may be either machined or made by injection molding, as described previously.

The gasket member 103" preferably comprises the anterior peripheral surface, or interface portion 108" and the inner anterior peripheral surface 109" both as described previously. As further shown in FIG. 8*a*, the anterior peripheral surface 108" is shaped in a spherical, or toric, fashion so as to be adapted to receive the posterior peripheral surface area 164 of the spherical outer lens 101, and the inner anterior peripheral surface 109" is shaped so as to be adapted in a cylindrical fashion to receive the posterior peripheral cylindrically-shaped surface area 168 of the cylindrical inner lens 102 in the cases where a non-heated embodiment is required.

Similar to that described in connection with the first embodiment above and fourth embodiment below in connection with FIGS. 4*a*, 9*a*-9*b*, 10*b*, 11*b*-11*g* and 12*b*, a plurality of spring snap members 407 and receptacles 409 may be employed to further secure interconnection of the eye-shield member 100" to the goggle frame member 212".

Fourth Embodiment

Referring to FIGS. 6*a*-6*d*, 7*e*-7*f*, 8*b*, 9*b*, 10*b*-10*c*, 11*h*-11*i* and 12*a*-12*b*, in a fourth embodiment of the invention, there is provided a multi-pane, multi-geometry eye-shield 100''' adapted for heating with a power source 229, such as for example a lithium-ion battery, carried for example on a goggle frame, a goggle strap, another eye-shield frame or on a user's person. Just as with eye-shield 100, 100' and 100", eye-shield 100''' also comprises a spherical, or toric, anterior outer eye-shield member 101 preferably made of a suitable optical grade plastic that is transparent and translucent, such as polycarbonate plastic. Eye-shield member 101 may be either machined or made by injection molding and has an anterior convex substantially spherical surface area 104 and a substantially spherical anterior peripheral surface area 162. The eye-shield member 101 further comprises a posterior concave substantially spherical, or toric, surface area 105 and a posterior substantially spherical peripheral surface area 164. On each side or end 120, 121 of outer eye-shield member 101, there is a hole 124, 125, each hole formed by a loop or band 122, 123 of resilient, semi-rigid lens material at or near the end of the eye-shield, or lens, 101, serving as a portion of an interconnection mechanism 126, 127.

Similar to the eye-shield 100, 100', 100" of previously described embodiments of the invention, the eye-shield 100''' of the fourth embodiment of the invention further comprises a cylindrical posterior inner eye-shield member 102' which is preferably made of a suitable optical grade plastic that is transparent and translucent, such as polycarbonate plastic. Inner eye-shield member 102' may be either machined or made by injection molding and has an anterior convex cylindrical surface area 106' and an anterior convex cylindrical peripheral surface area 166'. Inner eye-shield member 102' further comprises a posterior concave cylindrical surface area 107' and a posterior concave cylindrical peripheral surface area 168'. Cylindrical posterior inner eye-shield member 102' further comprises ends 140', 141', a peripheral edge 298', an upper portion 288' and a lower nose-bridge portion 289'.

Unlike inner eye-shield member 102, attached preferably to the anterior convex cylindrical surface 106' of the cylindrical posterior inner eye-shield member 102', there is a thin-film, electrically conductive heater 114, preferably made of a translucent, conductive material, such as Indium Tin Oxide (ITO). The conductive heater 114 is preferably applied by a process, such as where an ITO-coated polyester film is adhered to a polycarbonate lens with an optically clear adhesive, or where ITO is applied directly onto a polycarbonate lens by ion sputtering. In either case, only a very thin and uniform thickness of ITO (on the order of 800 angstroms, or 80 nanometers, thick) across the surface 106' is required. Of course, it will be appreciated by those of ordinary skill in the art that other available translucent, conductive heater materials may be used without departing from the true scope and spirit of the invention.

The cylindrical posterior inner eye-shield member 102' additionally has a plurality of electrical contact members 115, 116 made from an electrically conductive material, located preferably near the perimeter and near the ends 140', 141' of eye-shield member 102', and preferably on the anterior surface 106' of the inner eye-shield member 102'. Electrical contact members 115, 116 are adapted for interconnecting the heating member 114 and a power source. Interconnecting the electrical contact member 115, 116 with the thin-film heater 114, there are provided a plurality of bus bars 501, 502 included on the upper and lower portions 288', 289', respectively of cylindrical inner eye-shield member 102'. In greater detail, contact members 115, 116 comprise a hole on the eye-shield 102' and a contact rivet, in essence, as part of the remainder of the contact or circuit (e.g., contacts 112, 113, or contacts 112', 113').

The goggle eye-shield 100''' further comprises a gasket member 103''', preferably made of plastic, silicone, or another resilient material, located posterior of both the anterior spherical eye-shield member 101 and the posterior/inner cylindrical eye-shield member 102'. When assembled, the gasket member 103''', anterior spherical eye-shield member 101 and posterior cylindrical eye-shield member 102' define and form a water-tight and air-tight semi-annular space 450''' therebetween as illustrated in FIG. 12b. The gasket member 103''' has an anterior peripheral spherical, or toric, convex surface 108''' shaped so as to be adapted to interface to the concave posterior peripheral surface area 164 of the spherical, or toric, anterior eye-shield member 101, preferably such that the interface between the concave posterior surface area 105 and the anterior peripheral surface 108''' form a water-tight and air-tight seal 451''', as seen in FIG. 12b, around the perimeter edges of surfaces 164 and 108'''.

The gasket member 103''' also has an anterior inner peripheral cylindrical convex surface 109''' adapted for interfacing to the concave posterior cylindrical peripheral surface area 168' of the cylindrical posterior eye-shield member 102'. Preferably the concave posterior cylindrical peripheral surface area 168' and the anterior convex inner cylindrical surface peripheral area 109''' interface to form a water-tight and air-tight seal 452''' as seen in FIG. 12b, adjacent the peripheral edges of surfaces 168' and 109'''. Adhesive (not shown) may be used to help establish the aforementioned air-tight and water-tight seals. On each end 130''', 131''' of gasket member 103''', there is a hole 134''', 135''' each formed by a loop or band 132''', 133''' of resilient, semi-rigid gasket material at or near the end of gasket member 103''', serving as a portion of an interconnection mechanism 126, 127 (see FIG. 2b). The gasket member 103''' further comprises a posterior peripheral area, structure or lip 209''' that resides in a channel, or groove portion 308''' of a frame or body member 212''' of the goggle 200'''.

The gasket member 103''' also has a plurality of contact members 110''', 111' located at an end of electrically conductive material comprising a spring member 112', 113' at either end 130''', 131''' of the gasket 103''' located preferably on the inner upper and lower surfaces of each of the loops/bands 132''', 133''', respectively. The contacts 115, 116, 110', 111' are adapted for interconnecting the heating member 114 and the power source 229. Spring members 112', 113' serve as part of interconnection mechanism 126, 127 since they interconnect the heating member 114 of the eye-shield 101''' and the power source 229.

Referring now to FIGS. 4a, 9a-9b, 10b, 11b-11g and 12b, the gasket member 103''' further comprises a plurality of spring snap members 407 preferably integrally formed with the gasket member and positioned at multiple locations around the posterior periphery of the gasket member. Corresponding to each spring snap member 407, there is provided a receptacle 409, each receptacle being located at a corresponding location around the anterior periphery of the goggle frame 212''', each receptacle being adapted for receipt and retention, by containing and spring force retention of each spring snap member on a catch portion 411 of each receptacle, so as to be adapted to retain the eye-shield 100''' on the goggle frame 212'''. These spring snap members 407 and receptacles 409 enable a user to position and retain the eye-shield member 100''' on the goggle frame 212''', so as to allow easy installation and removal of the eye-shield from the goggle frame in a minimum number of steps, while at the same time allowing interconnection of the eye-shield 100''' with the posts 214', 215' of the goggle frame 212''', such that the loops/bands comprising interconnection mechanism 122, 123, 132''', 133''', 126, 127 (see FIG. 2b) serve to reinforce attachment of the eye-shield 100''' to the goggle frame 212'''.

Loop/band interconnection mechanism 122, 123, 132''', 133''', 126, 127 preferably further comprises an extent portion 210 at the furthest extent of the loop/band to facilitate easy grabbing, installation and removal of the loop/band interconnection mechanism from the goggle frame 212'''. Preferably, the loop/band interconnection mechanism 122, 123, 132''', 133''', 126, 127 comprises an integral extension of the same material forming the lens 101''' and gasket member 103''', formed in laminate fashion together with the inner lens 102' as well. It will be appreciated that the inner lens 102' may or may not have such a loop/band interconnection mechanism portion.

Goggle Body

While the combined spherical/cylindrical eye-shields of the present invention is interchangeable any of a number of body types and interconnection mechanisms, preferred goggle body's and interconnection mechanisms are shown and described. It will be appreciated that different types of goggle bodies, or eye-shield frame apparatus, may be employed without departing from the true scope and spirit of the invention pertaining to spherical/cylindrical composite eye-shields.

Referring to FIG. 5a, the body 212 of the goggle 200 is preferably made of plastic that is semi-flexible, but resilient, such as silicone, polycarbonate or other plastic and may be made by injection molding or machining. At each end 317, 319 of the goggle frame 212, there is provided a base member 313, 315, respectively. Each base member 313, 315 preferably provides a base for a post 214, 215, respectively. The base members 313, 315 may either be separate components able to be retained within or attached on the frame 212, or alternatively the base members may be an integral part of the frame. Each post 214, 215 has a channel 314, 316, respectively, formed around the post and adapted to receive and retain corresponding semi-rigid loop/bands 122, 123, 132, 133, respectively. Each post 214, 215 and an exterior portion of the base member 313, 315 comprise a seat area 283, 285 forming part of the interconnection mechanism 126, 127 (shown generally in FIG. 2a). The eye-shield 100 is adapted for engaging the semi-rigid anterior portion of the body 212 a distance from the user's eyes so as to provide a shield to the eyes.

A textile strap portion 310 is provided for assisting with retention of the goggle on a user's head or helmet. Depending from each end 317, 319 of the goggle body 212, the goggle 200 further comprises a rubber or silicone strap extension member/wing 321, 323, respectively for providing alternatively proper fit of the goggle on a user's head with, or without, a helmet. When a helmet is preferably worn, for safety reasons to prevent serious injury or death while participating in winter sports or other dangerous activities, the extension members/wings 321, 323 fan or otherwise extend outwardly to allow reduced tension of the strap 310 as it extends transversely of the goggle frame and around the helmet. The strap 310 comprises an articulating member 301 having an ability to tighten or loosen, to accommodate the greater width of the sides of a helmet.

Preferably, the frame 212 of the goggle 200 is of a durometer and flexibility to allow slight flexing of the frame, and the composite lens eye-shield structure 100 is of a flexibility that allows slight flexion to permit installation of the eye-shield onto the posts 214, 215 such that the loops/bands 122, 123, 132, 133, comprising at least part of the interconnection mechanism 126, 127 (see also FIG. 2a), serve to attach the eye-shield 101 to the posts 214, 215.

Upon flexing the eye-shield 100 to cause loops/bands 122, 123, 132, 133 to pass around their respective posts 214, 215, engagement of the eye-shield 100 on the goggle body 212 is assured. Similarly, simultaneously upon removal or disengagement of the eye-shield 100, the eye-shield is disconnected or disengaged from the goggle body 212. Also, simultaneously upon installation, as the eye-shield 100 is engaged on the goggle frame 212, a posterior peripheral area 209 (which may have a slight protrusion or tongue-like shape) of the gasket member 103 engages groove-like area 308 of the frame 212. Accordingly, the user is enabled to easily interchange lenses on the slopes from one lens type to another. For example, this feature may be employed to change from a clear lens used on a cloudy day to a tinted lens when the sun comes out.

Traditional vents 375, as well as foam vent covers 376, are provided also to help resist fogging of the eye-shield 100 of the goggle 200. The goggle 200 further comprises a posterior foam rubber interface member 224 attached to a posterior portion of the goggle body 212, such as by gluing, providing a comfortable interface of the goggle 200 on a user's face.

Figure 5B:
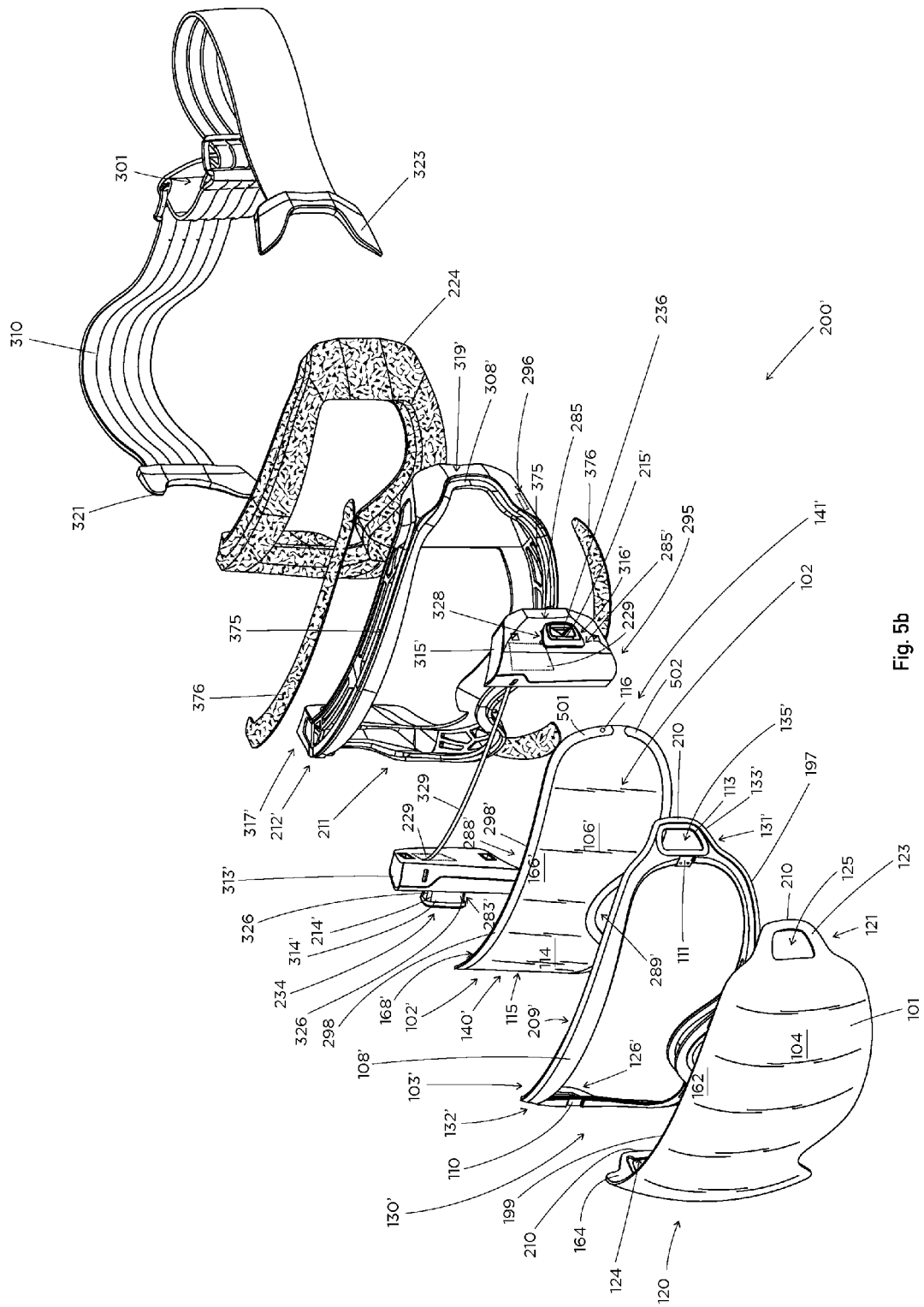
FIG. 5b yet another embodiment is an exploded perspective view of an embodiment of the invention adapted for heating and as implemented in a multi-pane, multi-geometry goggle eye-shield.
Figure 7D:
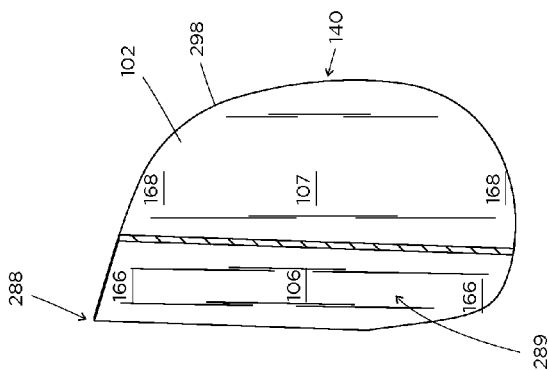
FIG. 7d is a right-side perspective section view of the cylindrical eye-shield of FIGS. 7a and 7b, cut on a plane, different than that of FIG. 7c, through a portion of the cylindrical eye-shield adapted to be located over a user's left eye.
Figure 7C:
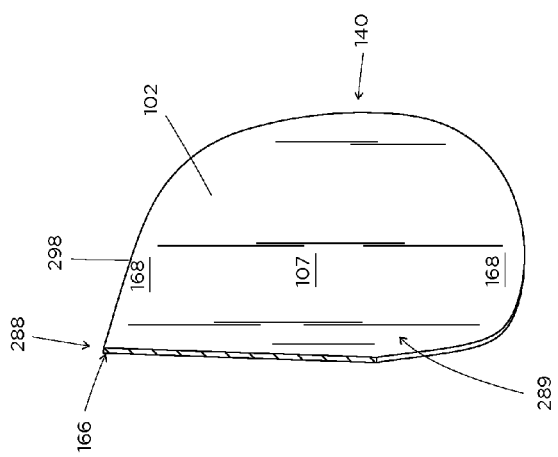
FIG. 7c is a right-side perspective section view of the cylindrical eye-shield of FIGS. 7a and 7b, cut on a sagittal plane through a portion of the cylindrical eye-shield adapted to be located above, and adjacent, a user's nose.
Figure 7B:
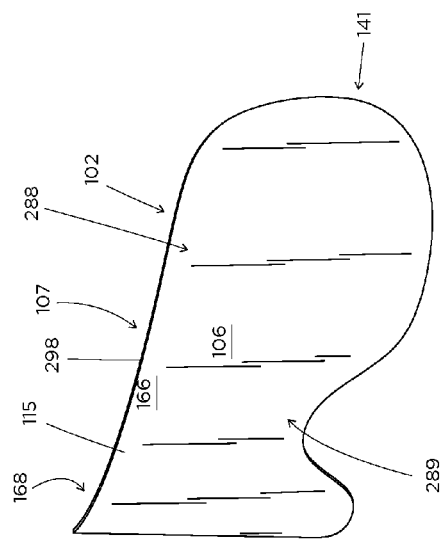
Figure 7A:
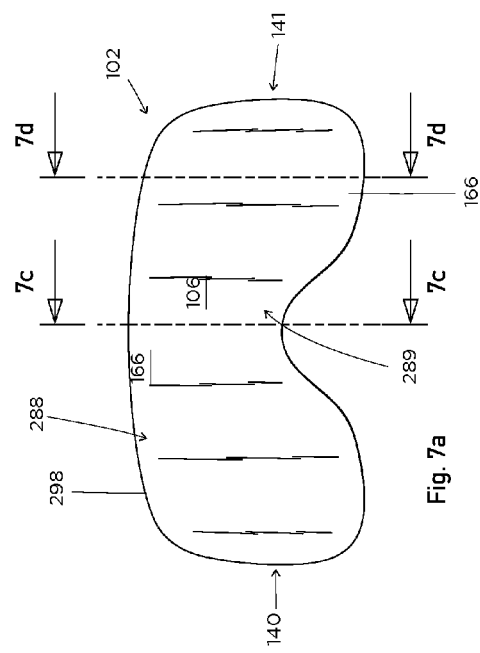
FIG. 7a is a front perspective view of an embodiment of a cylindrical eye-shield not adapted for heating of the cylindrical eye-shield.
Figure 7E:
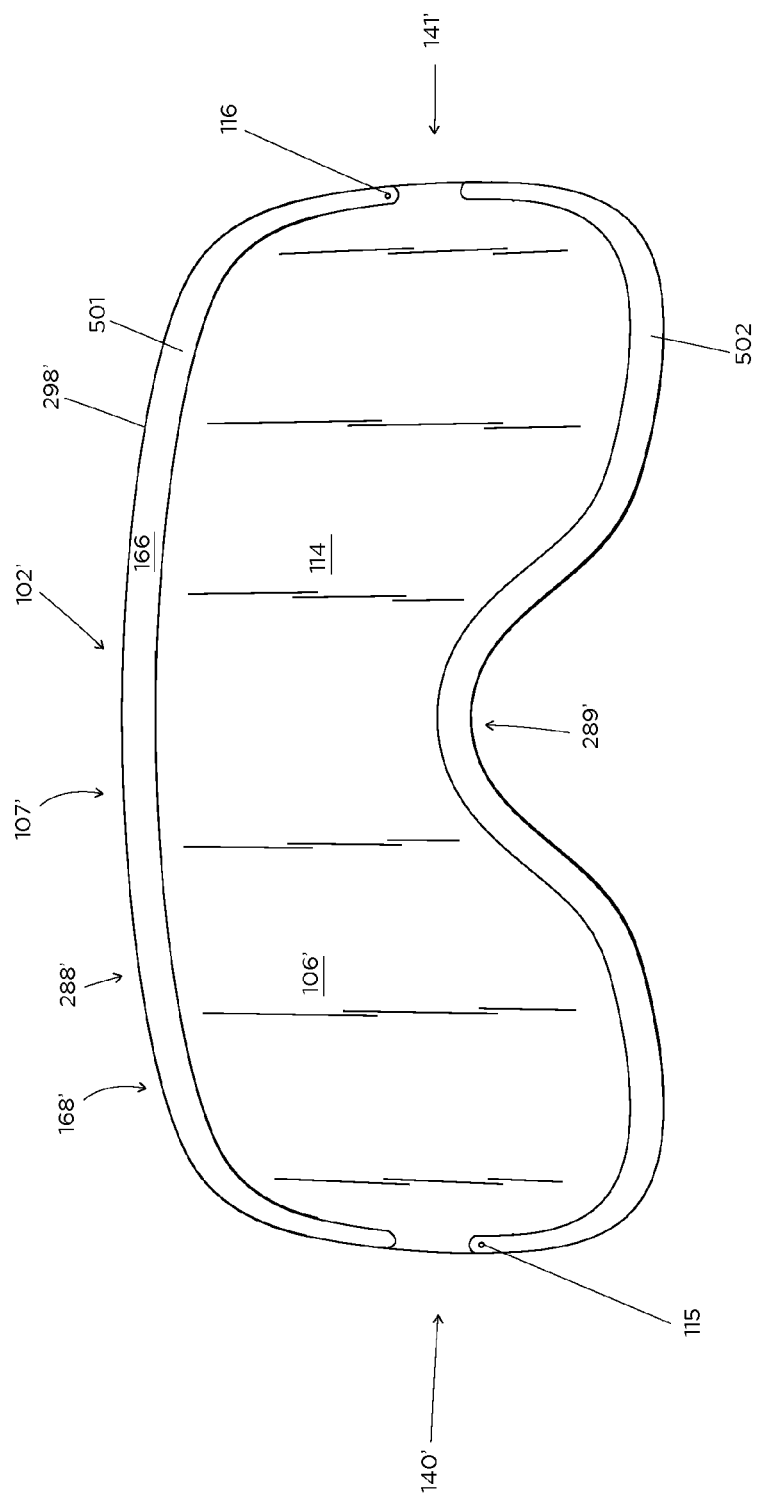
FIG. 7e is a front perspective view of an embodiment of a cylindrical eye-shield adapted for heating of the cylindrical eye-shield.
Figure 7F:
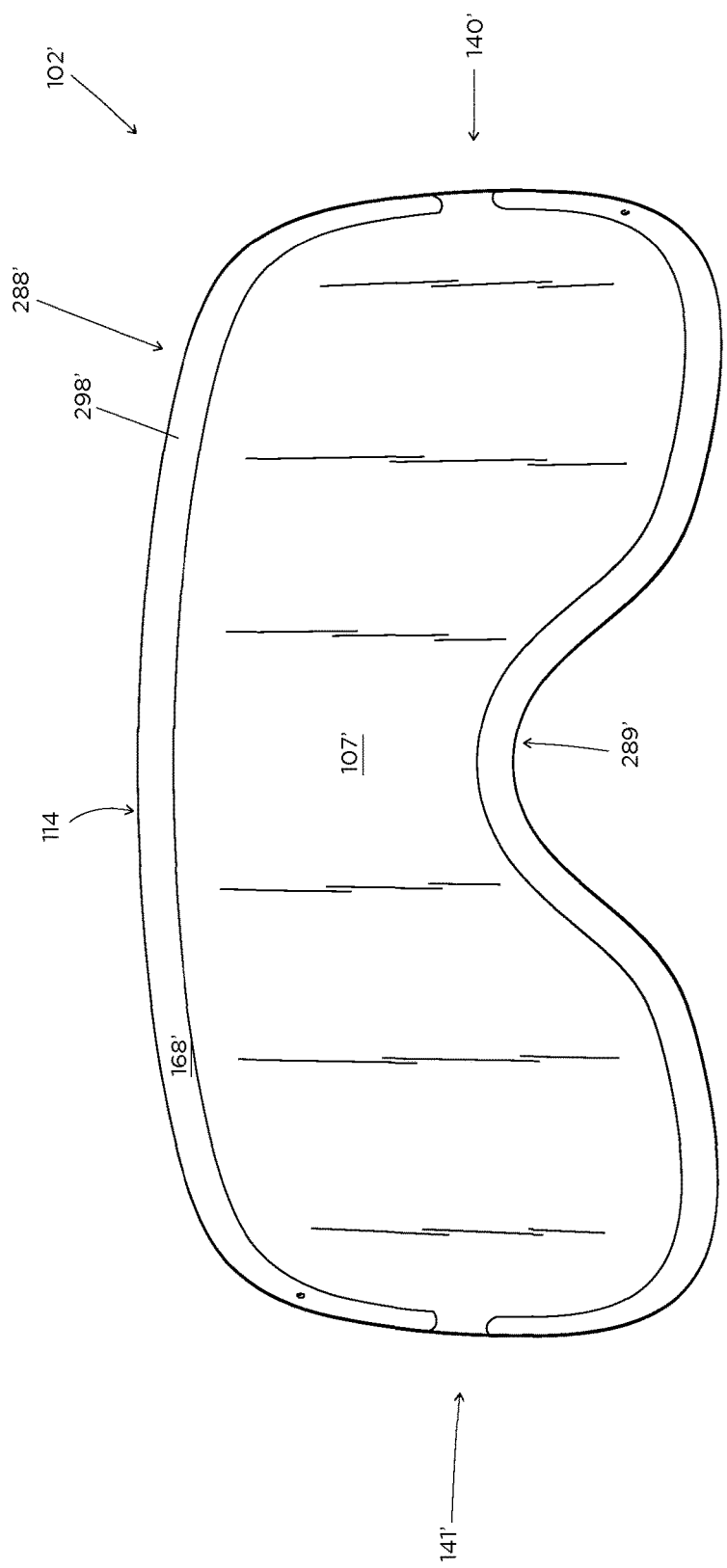
FIG. 7f is a rear perspective view of the cylindrical eye-shield of FIG. 7e.

Referring to FIG. 5b, the peripheral body, or goggle from member 212' of the goggle 200' is preferably made of plastic that is semi-flexible, but resilient, such as silicone, polycarbonate or other plastic and may be made by injection molding or machining. At each end 317', 319' of the goggle frame 212', there is provided a sealed, water-tight housing 313', 315', respectively, for retaining the electronics (e.g. circuit board 488 and circuit wires 330 of FIGS. 10b and 10c) and batteries 229 for the goggle 200'. The housings 313', 315' may either be separate components able to be retained within or attached on the frame 212', or alternatively the housings may be an integral part of the frame. On each electronic and battery housing 313', 315' of the plastic body 212', is a post 214', 215', respectively, each post having a channel 314', 316', respectively, formed around the post and adapted to receive and retain corresponding semi-rigid loop/bands 122, 123, 132', 133', respectively. Each post 214', 215' and an exterior portion of the housing 313', 315' comprise a seat area 283', 285' forming part of the interconnection mechanism 126, 127 (see also FIG. 2b). At one or more locations around each of the posts 214', 215', there are provided contacts for interconnecting with contact rings 112, 113. The eye-shield lens 100' is adapted for engaging the semi-rigid anterior portion of the body 212' a distance from the user's eyes so as to provide a shield to the eyes. The goggle body 212' preferably comprises a plurality of corresponding contacts 326, 328, preferably a pair located at upper and lower corresponding locations on posts 214', 215'.

Depending from each end 317', 319' of the goggle body 212', the goggle 200' further comprises a rubber or silicone strap extension member/wing 321, 323, respectively for providing alternatively proper fit of the goggle on a user's head with, or without, a helmet. When a helmet is preferably worn, for safety reasons to prevent serious injury or death while participating in winter sports or other dangerous activities, the extension members/wings 321, 323 fan or otherwise extend outwardly to allow reduced tension of the strap 310 as it extends transversely of the goggle frame and around, the helmet. The strap 310 comprises an articulating member 301, giving a user the ability to tighten or loosen the strap, to accommodate the greater width of the sides of a helmet.

Preferably, the frame 212' of the goggle 200' is of a durometer and flexibility to allow slight flexing of the frame, and the composite lens eye-shield structure 100' is of a flexibility that allows slight flexion to permit installation of the eye-shield onto the posts 214', 215' such that the bands or loops comprising interconnection mechanism 122, 123, 132', 133', 126, 127 serve to attach the eye-shield to the posts 214', 215'.

Upon flexing the bands/loops 122, 123, 132', 133' around their respective posts 214', 215', engagement of the lens frame 100' on the goggle body 212' is assured, and an electrical connection is made between the resistive-film anti-fog means 114 and batteries 229 preferably carried internally of the goggle body 212', as in housings 313', 315', or alternatively on the strap 310 or carried in the users' clothing. The electrical connection is made simultaneously upon installation of the lens frame 100' on the goggle body 212' via contacts 110', 111', contact rings 112, 113 on the loop/bands 132', 133' and contacts 326, 328 on the posts 214', 215', respectively, of the electronics and battery housings 313', 315' of the goggle body 212'. Nevertheless, it will be appreciated that there still may exist a need to turn on a switch or press a button as later described, for power to flow from the battery 229 to the heater 114. Also, simultaneously upon installation, as the eye-shield 100' is engaged on the goggle frame 212', with a posterior peripheral area 209' of the gasket member 103' engaging the groove-like area 308' of the frame 212', the contacts 112, 113 are simultaneously engaged with the power source of the goggle 200'. Similarly, simultaneously upon removal or disengagement of the eye-shield 101', the contacts 112, 113 are simultaneously disengaged with the power source 229 as the eye-shield is disconnected or disengaged from the goggle body 212'. Accordingly, the user is enabled to easily interchange lenses on the slopes from one lens type to another. For example, this feature may be employed to change from a clear lens used on a cloudy day to a tinted lens when the sun comes out.

Traditional vents 375, as well as foam vent covers 376, are also preferably provided to help conserve battery life, in the event of complete discharge of batteries or in the event a non-heated lens is employed with the goggle 200'. The goggle 200' further comprises a posterior foam rubber interface member 224 attached to a posterior portion of the goggle body 212', such as by gluing, providing a comfortable interface of the goggle 200' on a user's face. A textile strap portion 310 with an adjusting mechanism 301 is provided for assisting with retention of the goggle on a user's head or helmet.

Goggle 200' further comprises a button 234, 236 on each of the housings 313', 315' of, or on, the goggle body 212'. The buttons 234, 236 preferably on posts 214', 215', respectively, are for controlling on/off and/or heat level of the anti-fog means 114 on the lens 102'. Upon depressing the on/off button 234, heat source 229 may be switched on. Alternatively, a battery-strength indicator (not shown), and a heat, or power level, indicator (not shown) may be displayed preferably within the goggle 200' to the user of the goggle. Light pipes (not shown) may be used internal of each button 234, 236 to glow within the button to give visual cues to the user and others that the goggle is powered on and working. Depressing the on/off button 234 again may turn off the heat, or more accurately, may reduce it to an extremely low power state. Depressing the button 236 may be used to adjust the power level applied to the anti-fog means 114, and also may cause the power level display to indicate the level of power being applied to the anti-fog means. After a short time, preferably, the indicators turn off so as to not unduly distract the user. The circuitry of the goggle, interconnects a standard USB or other power connector charging receptacle 295 (extending through orifice 296 in frame 212'), to the battery 229, and interconnects the logic for controlling power on/off, power level increase/decrease, power level indication, and battery level indication using electric light pipes.

Referring to FIG. 8a, the body 212" of the goggle 200" is preferably made of plastic that is semi-flexible, but resilient, such as silicone, polycarbonate or other plastic and may be made by injection molding or machining. At each end 317", 319" of the goggle frame 212", there is provided a base member 313, 315, respectively. Just as with the base members 313, 315 of goggle 200, each base member 313, 315 of goggle 200" preferably provides a base for a post 214, 215, respectively. The base members 313, 315 may either be separate components able to be retained within or attached on the frame 212", or alternatively the base members may be an integral part of the frame. Each post 214, 215 has a channel 314, 316, respectively, formed around the post and adapted to receive and retain corresponding semi-rigid loop/bands 122, 123, 132", 133", respectively. Each post 214, 215 and an exterior portion of the base member 313, 315 comprise a seat area 283, 285 forming part of the interconnection mechanism 126, 127 (see also FIG. 2a). The eye-shield lens 100" is adapted for engaging the semi-rigid anterior portion of the body 212" a distance from the user's eyes so as to provide a shield to the eyes.

Depending from each end 317", 319" of the goggle body 212", the goggle 200" further comprises a rubber or silicone strap extension member/wing 321, 323, respectively for providing attachment of a strap 310 to the goggle frame 212" and providing alternatively proper fit of the goggle on a user's head with, or without, a helmet. When a helmet is preferably worn, for safety reasons to prevent serious injury or death while participating in winter sports or other dangerous activities, the extension members/wings 321, 323 fan or otherwise extend outwardly to allow reduced tension of the strap 310 as it extends transversely of the goggle frame and around the helmet. The strap 310 comprises an articulating member 301 having an ability to tighten or loosen, to accommodate the greater width of the sides of a helmet.

Preferably, the frame 212" of the goggle 200" is of a durometer and flexibility to allow slight flexing of the frame, and the composite lens eye-shield structure 100" is of a flexibility that allows slight flexion to permit installation of the eye-shield onto the posts 214, 215 such that the loops/bands comprising interconnection mechanism 122, 123, 132", 133", 126, 127 serve to attach the eye-shield structure 100" to the posts 214, 215.

Upon flexing the bands/loops 122, 123, 132", 133" around their respective posts 214, 215, engagement of the eye-shield 100" on the goggle body 212" is assured. Similarly, simultaneously upon removal or disengagement of the eye-shield 100", the eye-shield is disconnected or disengaged from the goggle body 212". Also, simultaneously upon installation, as the eye-shield 100" is engaged on the goggle frame 212", with a posterior peripheral area 209" of the gasket member 103" engaging, or seating in, the area 308" of the frame 212". Accordingly, the user is enabled to easily interchange lenses on the slopes from one lens type to another. For example, this feature may be employed to change from a clear lens used on a cloudy day to a tinted lens when the sun comes out.

Traditional vents 375, as well as foam vent covers 376, are provided to help resist fogging of the eye-shield 100" of the goggle 200". The goggle 200" further comprises a posterior foam rubber interface member 224 attached to a posterior portion of the goggle body 212", such as by gluing, providing a comfortable interface of the goggle 200" on a user's face. Similar to other embodiments described previously, a textile strap portion 310 is provided for assisting with retention of the goggle on a user's head or helmet.

Figure 8B:
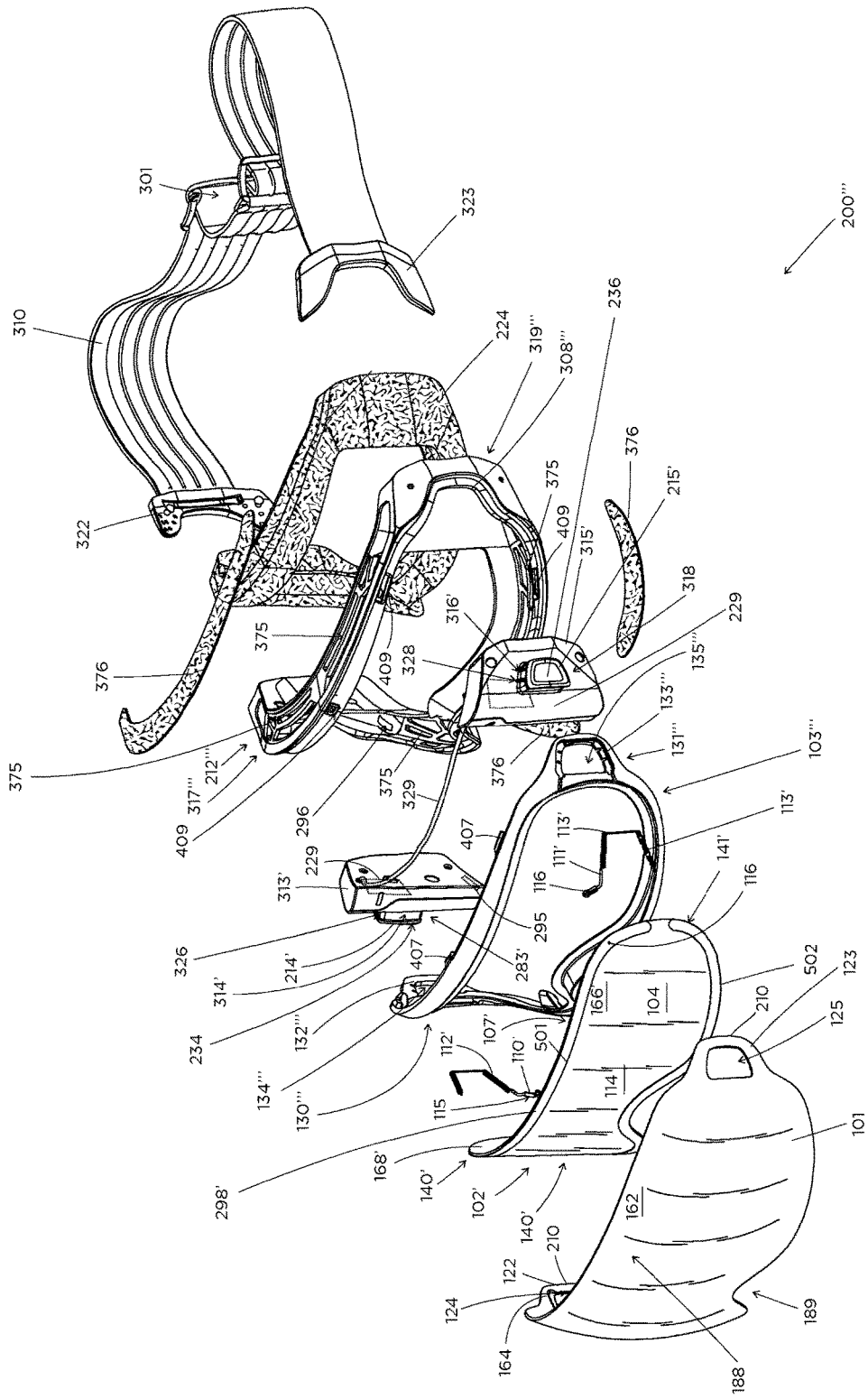
FIG. 8b is an exploded perspective view of still another alternate embodiment of the invention adapted for heating and implemented in a multi-pane, multi-geometry goggle eye-shield.

Referring to FIG. 8b, the peripheral body 212''' of the goggle 200''' is preferably made of plastic that is semi-flexible, but resilient, such as silicone, polycarbonate or other plastic and may be made by injection molding or machining. At each end 317''', 319''' of the goggle frame 212''', there is provided a sealed, water-tight housing 313', 315', respectively, for retaining the electronics and batteries 229 for the goggle 200'''. The housings 313', 315' may either be separate components able to be retained within or attached on the frame 212''', or alternatively the housings may be an integral part of the frame. On each electronic and battery housing 313', 315' of the plastic body 212''', is a post 214', 215', respectively, each post having a channel 314', 316', respectively, formed around the post and adapted to receive and retain corresponding semi-rigid loop/bands 122, 123, 132''', 133''', respectively. Each post 214', 215' and an exterior portion of the housing 313', 315' comprise a seat area 283', 285' to form part of the interconnection mechanism 126, 127 (see also FIG. 2b). At one or more locations around each of the posts 214', 215', there are provided contacts 326,328 for interconnecting with contact spring members 112', 113'. The eye-shield lens 100''' is adapted for engaging the semi-rigid anterior portion of the body 212''' a distance from the user's eyes so as to provide a shield to the eyes.

As described with previous embodiments, depending from each end 317''', 319''' of the goggle body 212''', the goggle 200''' further comprises strap extension members/wing 321, 323, respectively, for providing attachment of a strap 310 to the goggle frame 212''' and providing alternatively proper fit of the goggle on a user's head with, or without, a helmet.

Preferably, the frame 212''' of the goggle 200''' is of a durometer and flexibility to allow slight flexing of the frame, and the composite lens eye-shield structure 100''' is of a flexibility that allows slight flexion to permit installation of the eye-shield onto the posts 214', 215' such that the rings or loops comprising interconnection mechanism 122, 123, 132''', 133''', 126, 127 (see also FIG. 2b) serve to attach the eye-shield to the posts 214', 215'.

Upon flexing the bands/loops 122, 123, 132''', 133''' around their respective posts 214', 215', engagement of the eye-shield structure 100''', on the goggle body 212''' is assured, and an electrical connection is made between the resistive-film anti-fog means 114 and batteries 229 carried internally of the goggle body 212''', as in housings 313', 315', or alternatively on the strap 310 or carried in the users' clothing. The electrical connection is made simultaneously upon installation of the lens frame 100''' on the goggle body 212''' via contacts 110', 111', contact spring members 112', 113' partially embedded in the loop/bands 132''', 133''' and contacts 326, 328 on the posts 214', 215', respectively, of the electronics and battery housings 313', 315' of the goggle body 212'''. Also, simultaneously upon installation, as the eye-shield 100''' is engaged on the goggle frame 212''', with a posterior peripheral area 209''' of the gasket member 103''' engaging the groove-like area 308''' of the frame 212''', the spring contact members 112', 113' are simultaneously engaged with the power source 229 of the goggle 200'''. Similarly, simultaneously upon removal or disengagement of the eye-shield 101''', the spring contacts members 112', 113' are simultaneously disengaged with the power source 229 as the eye-shield is disconnected or disengaged from the goggle body 212'''. Accordingly, the user is enabled to easily interchange lenses on the slopes from one lens type to another. For example, this feature may be employed to change from a clear lens used on a cloudy day to a tinted lens when the sun comes out.

Traditional vents 375, as well as foam vent covers 376, are also preferably provided to help conserve battery life, in the event of complete discharge of batteries or in the event a non-heated lens is employed with the goggle 200'''. The goggle 200''' further comprises a posterior foam rubber interface member 224 attached to a posterior portion of the goggle body 212''', such as by gluing, providing a comfortable interface of the goggle 200''' on a user's face. A textile strap portion 310 is provided for assisting with retention of the goggle on a user's head or helmet.

Goggle 200''' further comprises a button 234, 236 on each of the housings 313', 315' of, or on, the goggle body 212'''. The buttons 234, 236 preferably on posts 214', 215', respectively, may be used for controlling on/off and heat level of the anti-fog means 114 on the lens 102'. Upon depressing the on/off button 234, heat source 229 may be switched on. Alternatively, a battery-strength indicator (not shown), and a heat, or power level, indicator (not shown), may be provided and displayed preferably within the goggle 200''' to the user of the goggle. Light pipes, not shown may be used internal of each button 234, 236 to glow within the button to give visual cues to the user and others that the goggle is powered on and working. Depressing the on/off button 234 again may turn off the heat, or more accurately may reduce it to an extremely low power state. Depressing the button 236 may be used to adjust the power level applied to the anti-fog means 114, and also may cause the power level display to indicate the level of power being applied to the anti-fog means. After a short time, preferably, the indicators turn off so as to not unduly distract the user. It will be appreciated that both buttons 234, 236, or just one button, may be employed.

The circuitry of the goggle 200''', similar to other embodiments disclosed herein, also interconnects a standard USB or other power connector charging receptacle 295 (extending through orifice 296 in frame 212'''), the battery 229 and interconnects the logic for controlling power on/off, power level increase/decrease, power level indication, and battery level indication using electric light pipes.

Figure 10B:
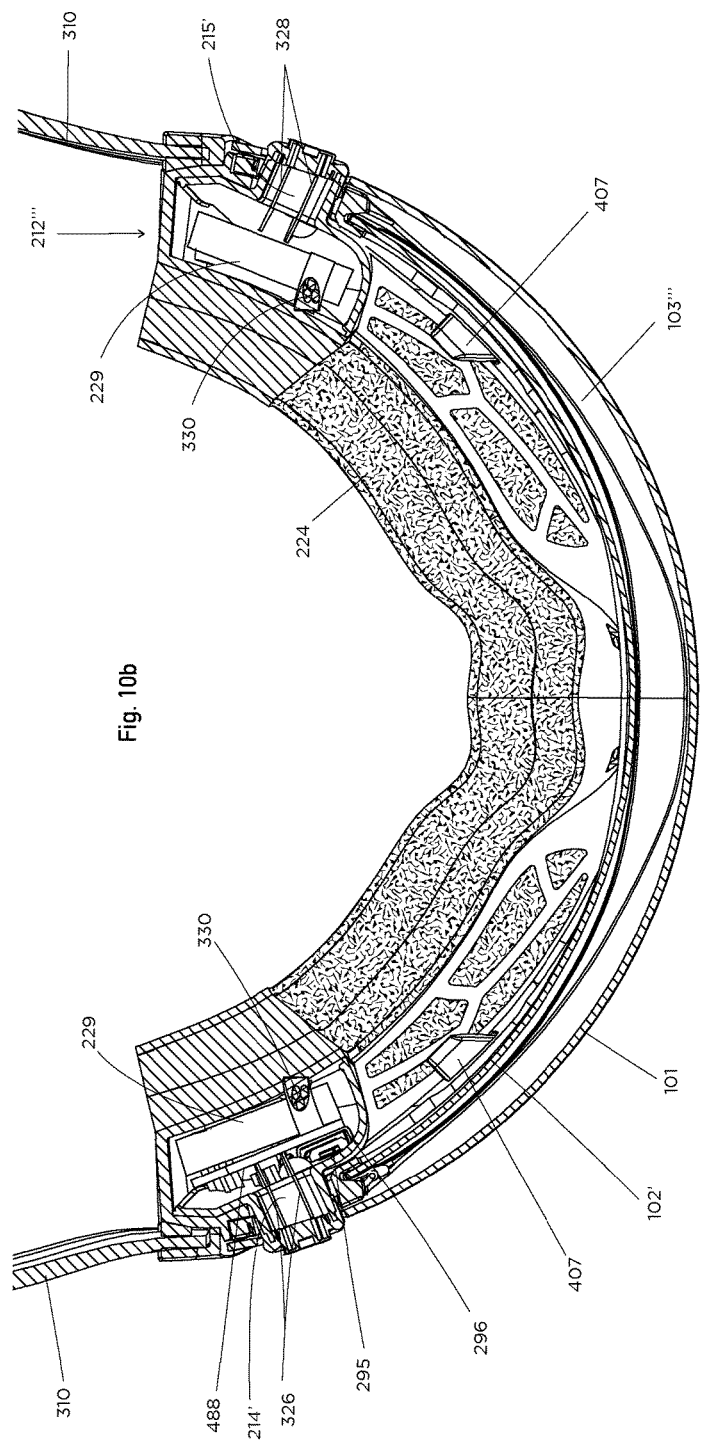
Figure 10A:
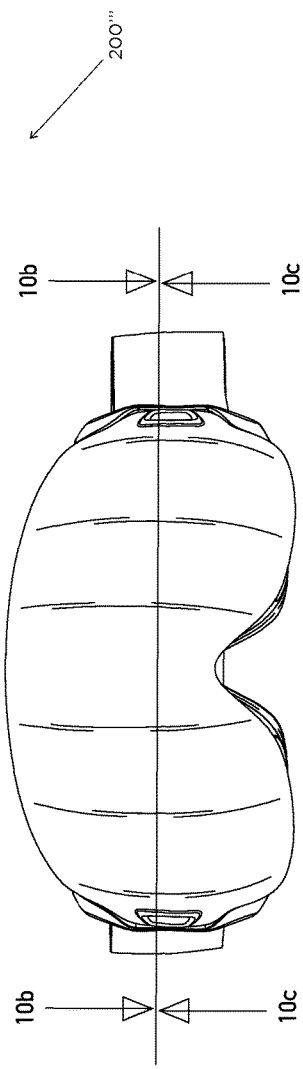
FIG. 10a is a front perspective view of a goggle in accordance with a heated embodiment of the invention.
Figure 10C:
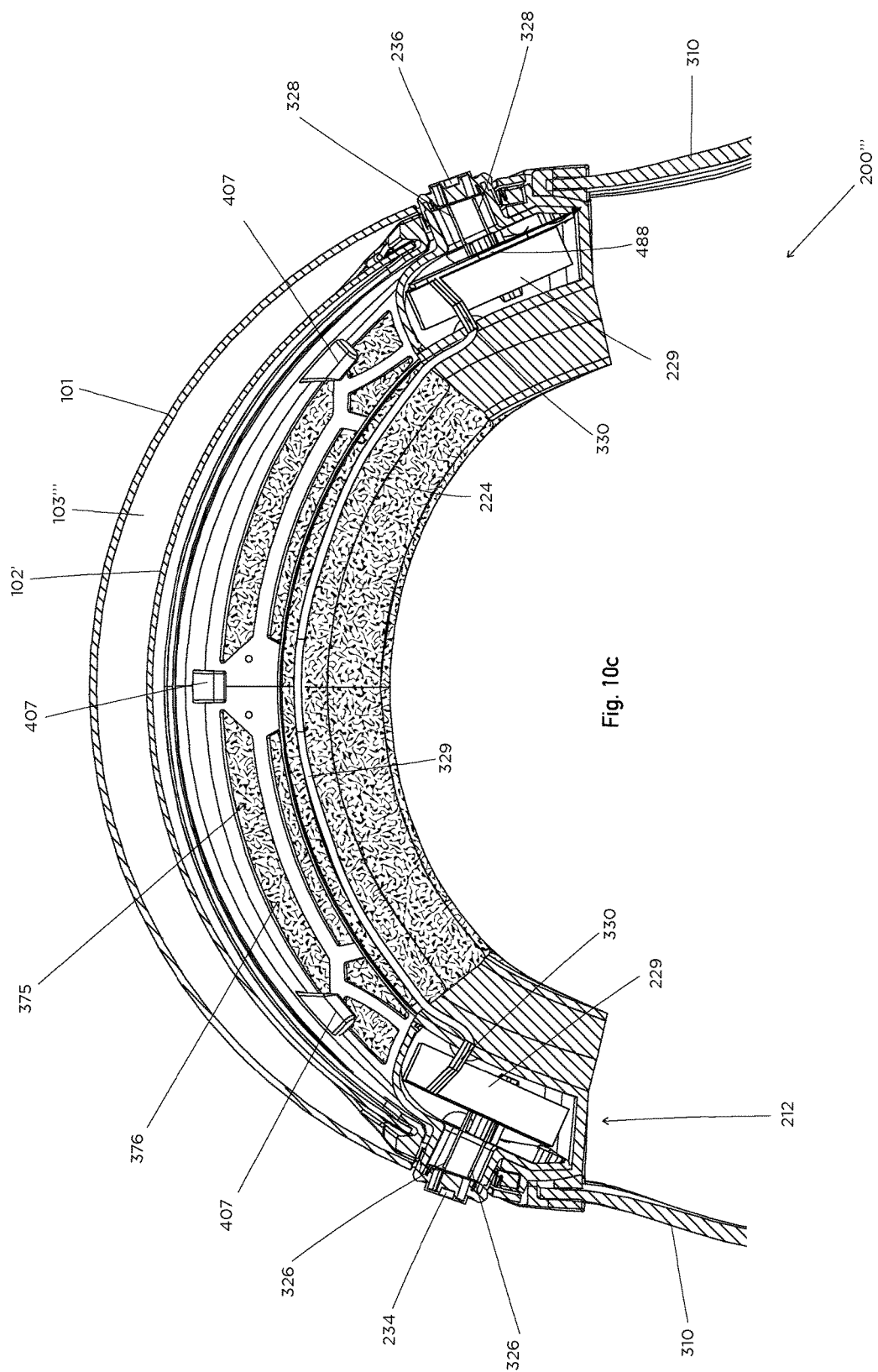
Figure 11H:
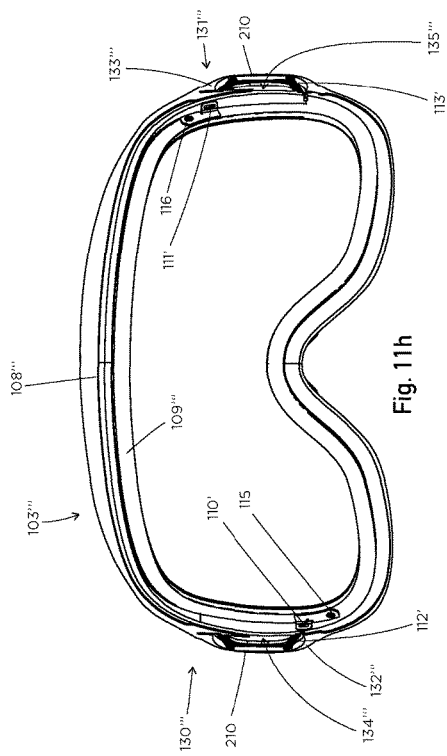
FIG. 11h is a front perspective view of an embodiment of a gasket in accordance with at least a portion of the invention adapted for heating.
Figure 11I:
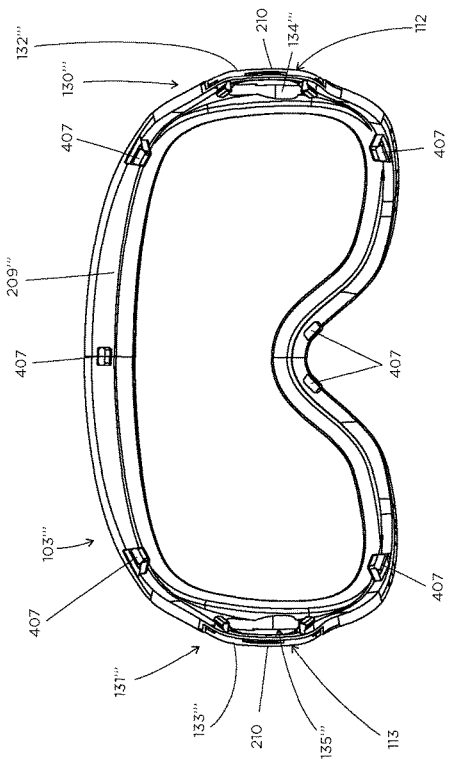
FIG. 11i is a rear perspective view of the gasket of FIG. 11h.
Figure 11G:
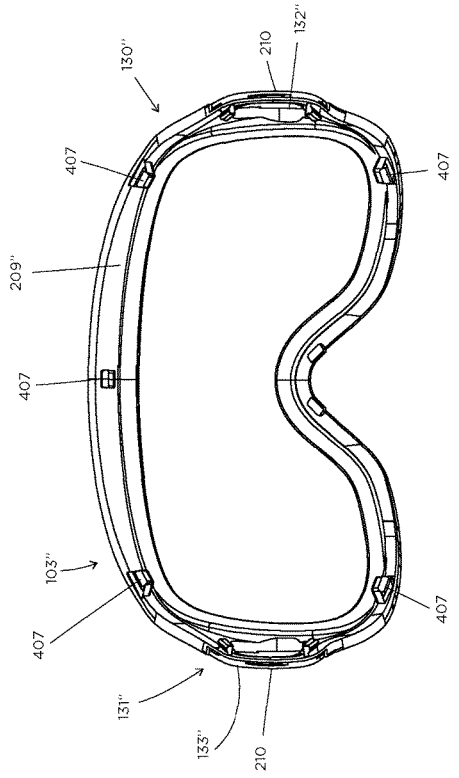
FIG. 11g is a rear view of the gasket of FIGS. 11a and 11b.

Referring to FIGS. 10a-10c, there is provided a more detailed showing of the goggle 200''' showing spring connectors 407, receptacles 409, outer spherical eye-shield 101, inner cylindrical eye-shield 102', goggle frame 212''', buttons 234, 236, circuit board 488, circuit wiring 329, 330, batteries 229, recharging receptacle 295 and orifice 296, posts 214', 215' with contacts 326, 328 thereon, foam interface 224 and gasket 103'''.

Figure 4A:
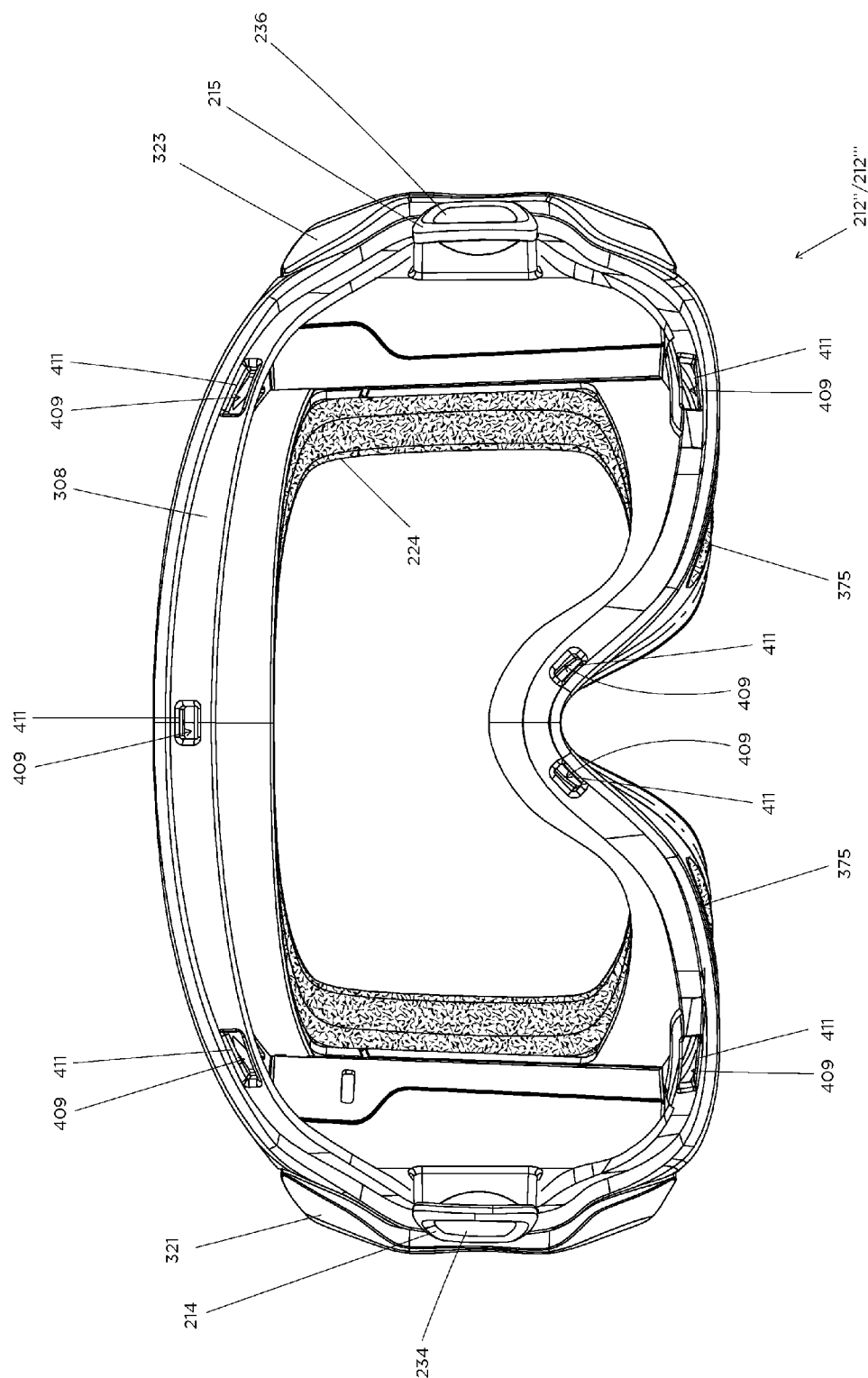
FIG. 4a is a front perspective view of an embodiment of a frame portion of a goggle adapted to receive a multi-pane, multi-geometry goggle eye-shield.

It may be seen in FIG. 4a that the plurality of receptacles 409 with catch portions 411 may be defined in surface 308 of the goggle body 212'', 212''' (or other embodiment of the goggle body) and spaced at intervals around the goggle body. It will be appreciated that the receptacles may be employed with any embodiment of the invention hereof, or not, depending upon the materials used and attachment characteristics desired. Similarly, the posts 214, 215 may either carry a button 234, 236, as shown for a heated embodiment comprising goggle body 212''', or no button in the case of a non-heated embodiment comprising goggle body 212''. Extension members/wings 321, 323, foam interface 224 and vents 375 with foam vent covers 376 may be employed with any of the embodiments of the invention.

Heating Embodiments

In accordance with the foregoing descriptions, there are provided two different embodiments of a multi-pane, multi-geometry eye-shield wherein the eye-shield of each is further adapted for heating. The devices of this heating aspect of the invention further comprises heating of the eye-shield and assists in providing a goggle or eye-shield mask that is fog and condensation resistant, or dew resistant, by raising the temperature of the surface of the eye-shield above that temperature at which condensation forms. Limiting the formation of condensation, or fogging, on a lens provides a safer and more enjoyable environment and experience for a wearer.

Further in accordance with this aspect of the invention relating to the multi-pane, multi-geometry eye-shield being adapted for being heated, the eye-shield adapted for heating further preferably comprises a heater attached to at least one of the eye-shield members. As shown and described, preferably the heater is attached to the anterior surface of the inner cylindrical eye-shield member. The device of this aspect of the invention of attaching a heater to one of the eye-shield members enables direct heating of the eye-shield. Directly heating the eye-shield additionally helps to effectively prevent fogging and condensation from forming on the eye-shield, creating a safer and more enjoyable environment for the wearer.

Still further in accordance with this aspect of the invention providing a multi-pane, multi-geometry eye-shield adapted for heating, an eye-shield adapted for heating with a heater attached to one of the eye-shields preferably comprises a thin-film, electrically conductive heater attached to the anterior convex surface of the cylindrical posterior inner eye-shield member, and a plurality of electrical contact members adapted for interconnecting the heater and a power source preferably carried on the eye-shield frame or strap. The thin-film heater of this aspect of the invention may, for example, preferably be comprised of a thin-film transparent heater such as may be made with Indium Tin Oxide (ITO) or other currently available thin-film heating material.

It will be appreciated that references herein to spherical, toric or cylindrical lenses, eye-shields or gasket surfaces, actually refer to a partial sphere, partial torus or partial cylinder on each of these elements, respectively, not that the elements comprise an entire sphere, torus or cylinder. Also, the term "spherical" is often used herein, but it will be appreciated that "toric" would also apply without departing from the true scope and spirit of the invention. Thus, the terms "spherical", "toric" and "cylindrical", as used herein, refer to the shape of the element at the given location being described, not that the element comprises an entire sphere, torus or cylinder.

While a preferred embodiment of the present invention has been shown and described, it will be apparent to those skilled in the art that many changes and modifications may be made without departing from the invention in its broader aspects. For example, it will be appreciated that one of ordinary skill in the art may mix, match, and alter various components of the embodiments of the invention without departing from the true scope and spirit of the invention as claimed. Thus, for example, it will be appreciated that the electrical systems and/or contacts of the second and fourth embodiments may be interchanged without departing from the true scope and spirit of the invention. Further, interchanging lens colors or disclosed multi-pane, multi geometry goggle eye-shields with an alternate embodiment body or lens frame would likewise not depart from the true spirit and scope of the invention. The appended claims are therefore intended to cover all such changes and modifications as fall within the true spirit and scope of the invention.

What is claimed is:

1. A multi-pane, multi-geometry eye-shield adapted to be installed into a frame of a goggle, comprising:
   A spherical anterior outer eye-shield member having an anterior convex substantially spherical surface and peripheral area and a posterior concave substantially spherical surface and peripheral area;
   A cylindrical posterior inner eye-shield member having an anterior convex substantially cylindrical surface and peripheral area and a posterior concave substantially cylindrical surface and peripheral area; and
   A gasket member interposed and sealed between the anterior and posterior eye-shield members forming a water-tight and air-tight semi-annular space therebetween, said gasket member having an anterior peripheral surface adapted for interfacing to the concave posterior surface peripheral area of said spherical anterior eye-shield member, said gasket member having a posterior peripheral surface adapted for interfacing to the convex anterior surface peripheral area of said cylindrical posterior eye-shield member, said gasket member further comprising a peripheral anterior surface and a peripheral posterior surface, wherein the normal distance between the peripheral anterior surface and the peripheral posterior surface of said gasket member varies along a peripheral length of said gasket member to accommodate shape variations in each the concave posterior surface peripheral area of said spherical anterior outer eye-shield member and the convex anterior surface peripheral area of said cylindrical posterior inner eye-shield member.

2. The eye-shield of claim 1, wherein said eye-shield is adapted for heating.

3. The eye-shield of claim 2, further comprising a heating member attached to one of said eye-shield members.

4. The eye-shield of claim 3, further comprising a thin-film, electrically conductive heater attached to the anterior convex surface of said cylindrical posterior inner eye-shield member; and a plurality of electrical contact members adapted for interconnecting said heating member and a power source.

5. The eye-shield of claim 4, wherein said plurality of electrical contact members communicate through said gasket member without compromising the water-tight or air-tight semi-annular space.

6. A multi-pane, multi-geometry eye-shield adapted for converting electrical power input into heating of the eye-shield, the eye-shield adapted to be installed into a frame of a goggle, comprising:
   A spherical anterior outer eye-shield member having an anterior convex substantially spherical surface and peripheral area and a posterior concave substantially spherical surface and peripheral area;
   A cylindrical posterior inner eye-shield member having an anterior convex substantially cylindrical surface and peripheral area and a posterior concave substantially cylindrical surface and peripheral area;
   A heating member attached to the anterior convex surface of said cylindrical posterior inner eye-shield member;
   A plurality of electrical contact members adapted for interconnecting said heating member and a power source; and
   A gasket member interposed and sealed between the anterior and posterior eye-shield members forming a water-tight and air-tight semi-annular space therebetween, said gasket member having an anterior peripheral surface adapted for interfacing to the concave posterior surface peripheral area of the spherical anterior eye-shield member, said gasket member having a posterior peripheral surface adapted for interfacing to the convex anterior surface peripheral area of the cylindrical posterior eye-shield member, said gasket member further comprising a peripheral anterior surface and a peripheral posterior surface, wherein the normal distance between the peripheral anterior surface and the peripheral posterior surface of said gasket member varies along a peripheral length of said gasket member to accommodate shape variations in each the concave posterior surface peripheral area of said spherical anterior outer eye-shield member and the convex anterior surface peripheral area of said cylindrical posterior inner eye-shield member.

7. The eye-shield of claim 6, wherein said plurality of electrical contact members communicate through said gasket member without compromising the water-tight or air-tight semi-annular space.

8. A multi-pane, multi-geometry eye-shield adapted to be installed into a frame of a goggle, comprising:
   A spherical anterior outer eye-shield member having an anterior convex substantially spherical surface and peripheral area and a posterior concave substantially spherical surface and peripheral area;
   A cylindrical inner eye-shield member having an anterior convex surface and peripheral area and a posterior concave surface and peripheral area; and
   A substantially posterior gasket member sealed to said spherical anterior outer eye-shield member and the cylindrical inner eye-shield member, said gasket member further comprising an outermost anterior, substantially spherical, peripheral surface adapted for interfacing to the concave posterior surface peripheral area of said spherical anterior outer eye-shield, said gasket member further comprising an inner anterior, substantially cylindrical, peripheral surface at least partially within the outermost anterior peripheral surface and adapted for interfacing to the posterior concave surface peripheral area of said cylindrical inner eye-shield member, said posterior gasket member being posterior to both said spherical anterior outer eye-shield and said cylindrical inner eye-shield, wherein the inner anterior, substantially cylindrical, peripheral surface of said substantially posterior gasket member is recessed relative to the outermost anterior, substantially spherical, peripheral surface of said substantially posterior gasket member such that the normal distance between the inner anterior, substantially cylindrical, peripheral surface and the outermost anterior substantially spherical peripheral surface varies along a peripheral length of said substantially posterior gasket member to accommodate shape variations in each the concave posterior surface peripheral area of said spherical anterior outer eye-shield member and the convex posterior surface peripheral area of said cylindrical posterior inner eye-shield member.

9. The multi-pane, multi-geometry eye-shield of claim 8, wherein said posterior gasket member forms a water-tight or air-tight semi-annular space between said spherical anterior outer eye-shield and said cylindrical inner eye-shield.

10. The multi-pane, multi-geometry eye-shield of claim 9, further comprising:
   a heating member attached to the anterior convex surface of said cylindrical inner eye-shield member; and a plurality of electrical contact members adapted for interconnecting said heating member and a power source; wherein the multi-pane eye-shield is adapted for converting electrical power input into heating of the multi-pane eye-shield to prevent fogging.

11. The eye-shield of claim 10, wherein said electrical contact members communicate through said gasket member without compromising the water-tight or air-tight semi-annular space.

* * * * *